US010750693B2

(12) United States Patent
Hirschberg et al.

(10) Patent No.: US 10,750,693 B2
(45) Date of Patent: Aug. 25, 2020

(54) TOMATO PLANTS HAVING FRUIT WITH YELLOW AND RED SEGMENTS

(71) Applicant: Yissum Research Development Company of the Hebrew University of Jerusalem Ltd., Jerusalem (IL)

(72) Inventors: Joseph Hirschberg, Jerusalem (IL); Dani Zamir, Gedera (IL); Yaacov Micha Brog, Rehovot (IL); Itay Zemach, Rehovot (IL); Orly Dery, Jerusalem (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 0 days.

(21) Appl. No.: 15/741,927

(22) PCT Filed: Jul. 5, 2016

(86) PCT No.: PCT/IL2016/050719
§ 371 (c)(1),
(2) Date: Jan. 4, 2018

(87) PCT Pub. No.: WO2017/006318
PCT Pub. Date: Jan. 12, 2017

(65) Prior Publication Data
US 2019/0021251 A1    Jan. 24, 2019

Related U.S. Application Data

(60) Provisional application No. 62/188,755, filed on Jul. 6, 2015.

(51) Int. Cl.
*A01H 5/08* (2018.01)
*A01H 1/00* (2006.01)
*A01H 6/82* (2018.01)

(52) U.S. Cl.
CPC .............. *A01H 5/08* (2013.01); *A01H 1/00* (2013.01); *A01H 6/825* (2018.05); *C12Y 205/01032* (2013.01)

(58) Field of Classification Search
None
See application file for complete search history.

(56) References Cited

PUBLICATIONS

Fernie et al., (2006) Natural genetic variation for improving crop quality. Current opinion in plant biology, 9(2), 196-202.
Fray et al., (1993) Identification and genetic analysis of normal and mutant phytoene synthase genes of tomato by sequencing, complementation and co-suppression. Plant molecular biology, 22(4), 589-602.
Giorio et al., (2008) Phytoene synthase genes in tomato (Solanumlycopersicum L.)—new data on the structures, the deduced amino acid sequences and the expression patterns. The FEBS journal, 275(3), 527-535.
Grandillo et al., (1996) QTL analysis of horticultural traits differentiating the cultivated tomato from the closely related species Lycopersicon pimpinellifolium. TAG Theoretical and Applied Genetics, 92(8), 935-951.
Tomaten et al., Orange Russian 117, Retrieved from the internet on Nov. 27 2016, URL: http://www.irinas-shop.de/orange-russian-117-p-529.html, 2 pages.
Kachanovsky et al., (2012) Epistasis in tomato color mutations involves regulation of phytoene synthase 1 expression by cis-carotenoids. Proceedings of the National Academy of Sciences, 109(46), 19021-19026.
Kang et al., (2014) A chimeric transcript containing Psy1 and a potential mRNA is associated with yellow flesh color in tomato accession PI 114490. Planta, 240(5), 1011-1021.
Kashkush et al., (2003) Transcriptional activation of retrotransposons alters the expression of adjacent genes in wheat. Nature genetics, 33(1), 102-106.
McClintock, (1984) The Significance of Responses of the Genome to Challenge. Science, 226, 792-801.
McCouch, (2004) Diversifying selection in plant breeding. PLoS biology, 2(10), e347, 1507-1512.
Menda et al., (2004) In silico screening of a saturated mutation library of tomato. The Plant Journal, 38(5), 861-872.
Ozkan et al., (2001) Allopolyploidy-induced rapid genome evolution in the wheat (Aegilops-Triticum) group. The Plant Cell, 13(8), 1735-1747.
Potrykus, (1991) Gene transfer to plants: assessment of published approaches and results. Annual review of plant biology, 42(1), 205-225.
Ronen et al., (1999) Regulation of carotenoid biosynthesis during tomato fruit development: expression of the gene for lycopene epsilon-cyclase is down-regulated during ripening and is elevated in the mutantDelta. The Plant Journal, 17(4), 341-351.
Shaked et al., (2001) Sequence elimination and cytosine methylation are rapid and reproducible responses of the genome to wide hybridization and allopolyploidy in wheat. The Plant Cell, 13(8), 1749-1759.
Shimamoto et al., (1989) Fertile transgenic rice plants regenerated from transformed protoplasts. Nature, 338(6212), 274-276.
Tanksley et al., (1997) Seed banks and molecular maps: unlocking genetic potential from the wild. Science, 277 (5329), 1063-1066.
Yuan et al., (2008) Genetics of flesh color and nucleotide sequence analysis of phytoene synthase gene 1 in a yellow-fruited tomato accession PI114490. Scientia horticulturae, 118(1), 20-24.
Zamir, (2001) Improving plant breeding with exotic genetic libraries. Nature reviews genetics, 2(12), 983-989.

*Primary Examiner* — Phuong T Bui
(74) *Attorney, Agent, or Firm* — J.A. Lindeman & Co. PLLC

(57) ABSTRACT

Provided are tomato plants having fruit with red and yellow segments that appear across the fruit from the internal seed area to the most external layer of the epidermis. The present invention discloses that this phenotype, designated Arlecchino, is linked to insertion mutation within the Phytoene synthase 1 (Psy1) gene.

13 Claims, 11 Drawing Sheets
Specification includes a Sequence Listing.

```
WT, M82 Fruit     → GTGGATCCTGAAATGGCTTGGATTGCTATTATTCTGGATA------------TGGCAAAAC SEQ ID NO:25
Arlecchino leaf   → GTGGATCCTGAAATGGCTTGGATTGCTATTATTCTGGATAATCTGGATAATGGCAAAAC SEQ ID NO:26
                    GTGGATCCTGAAATGGCTTGGATTGCTATTATTCTGGATAATCTGGATATGGCAAANC  SEQ ID NO:26
                    GTGGATCCTGAAATGGCTTGGATTGCTATTATTCTGGATAATCTGGATATGGCAAAAC  SEQ ID NO:26
                    GTGGATCCTGAAATGGCTTGGATTGCTATTATTCTGGATAATCTGGATATGGCAAAAC  SEQ ID NO:26
                    GTGGATCCTGAAATGGCTTGGATTGCTATTATTCTGGATAATCTGGATATGGCAAAAC  SEQ ID NO:26
                    GTGGATCCTGAAATGGCTTGGATTGCTATTATTCTGGATAATCTGGATATGGCAAAAC  SEQ ID NO:26
                    GTGGATCCTGAAATGGCTTGGATTGCTATTATTCTGGATAATCTGGATATGGCAAAAC  SEQ ID NO:26
Arlecchino fruit  ⎧ GTGGATCCTGAAATGGCTTGGATTACTATTATTCTGGATAATCTGGATATGGCAAAAC  SEQ ID NO:26
yellow sections   ⎨ GTGGATCCTGAAATGGCTTGGATTGCTATTATTCTGGATAATCTGGATATGGCAAAAC  SEQ ID NO:26
                  ⎩ GTGGATCCTGAAATGGCTTGGATTGCTATTATTCTGGATTCTGGAT---CTGGATA---------ATATGGCAAAAC SEQ ID NO:27
                    GTGGATCCTGAAATGGCTTGGATTGCTATTATTCTGGATATCCGGATA------ATATGGCAAAAC SEQ ID NO:28
                    GTGGATCCTGAAATGGCTTGGATTGCTATTATTCTGGATATCTGGATA------ATATGGCAAAAC SEQ ID NO:28
                    GTGGATCCTGAAATGGCTTGGATTGCTATTATTCTGGATATCTGGATA------ATATGGCAAAAC SEQ ID NO:29
                    GTGGATCCTGAAATGGCTTGGATTGCTATTATTCTGGATATCTGGATA------ATATGGCAAAAC SEQ ID NO:29
                    GTGGATCCTGAAATGGCTTGGATTGCTATTATTCTGGATATCTGGATA------ATATGGCAAAAC SEQ ID NO:28
                    GTGGATCCTGAAATGGCTTGGATTGCTATTATTCTGGATATCTGGATA------ATATGGCAAAAC SEQ ID NO:28
                    GTGGATCCTGAAATGGCTTGGATTGCTATTATTCTGGATATCTGGATA------ATATGGCAAAAC SEQ ID NO:28
                    GTGGATCCTGAAATGGCTTGGATTGCTATTATTCTGGATATCTGGATA------ATATGGCAAAAC SEQ ID NO:29
                    GTGGATCCTGAAATGGCTTGGATTGCTATTATTCTGGATATCTGGATA------ATATGGCAAAAC SEQ ID NO:29
Arlecchino fruit  ⎧ GTGGATCCTGAAATGGCTTGGATTGCTATTATTCCTGGATATCTGGATA------ATATGGCAAAAC SEQ ID NO:28
Red sections      ⎨ GTGGATCCTGAAATGGCTTGGATTGCTATTATTCTGGATAATCTGGATATGGCAAAAC  SEQ ID NO:26
                  ⎩ GTGGATCCTGAAATGGCTTGGATTGCTATTATTCTGGATAATCTGGATATGGCAAAAC  SEQ ID NO:26
                    GTGGATCCTGAAATGGCTTGGATTGCTATTATTCTGGATAATCTGGATATGGCAAAAC  SEQ ID NO:26
                    GTGGATCCTGAAATGGCTTGGATTGCTATTATTCTGGATAATCTGGATATGGCAAAAC  SEQ ID NO:26
                    GTGGATCCTGAAATGGCTTGGATTGCTATTATTCTGGATAATCTGGATATGGCAAAAC  SEQ ID NO:26
                    GTGGATCCTGAAATGGCTTGGATTGCTATTATTCTGGATAATCTGGATATGGCAAAAC  SEQ ID NO:26
                    GTGGATCCTGAAATGGCTTGGATTGCTATTATTCTGGATAATCTGGATATGGCAAAAC  SEQ ID NO:26
```

FIGURE 5

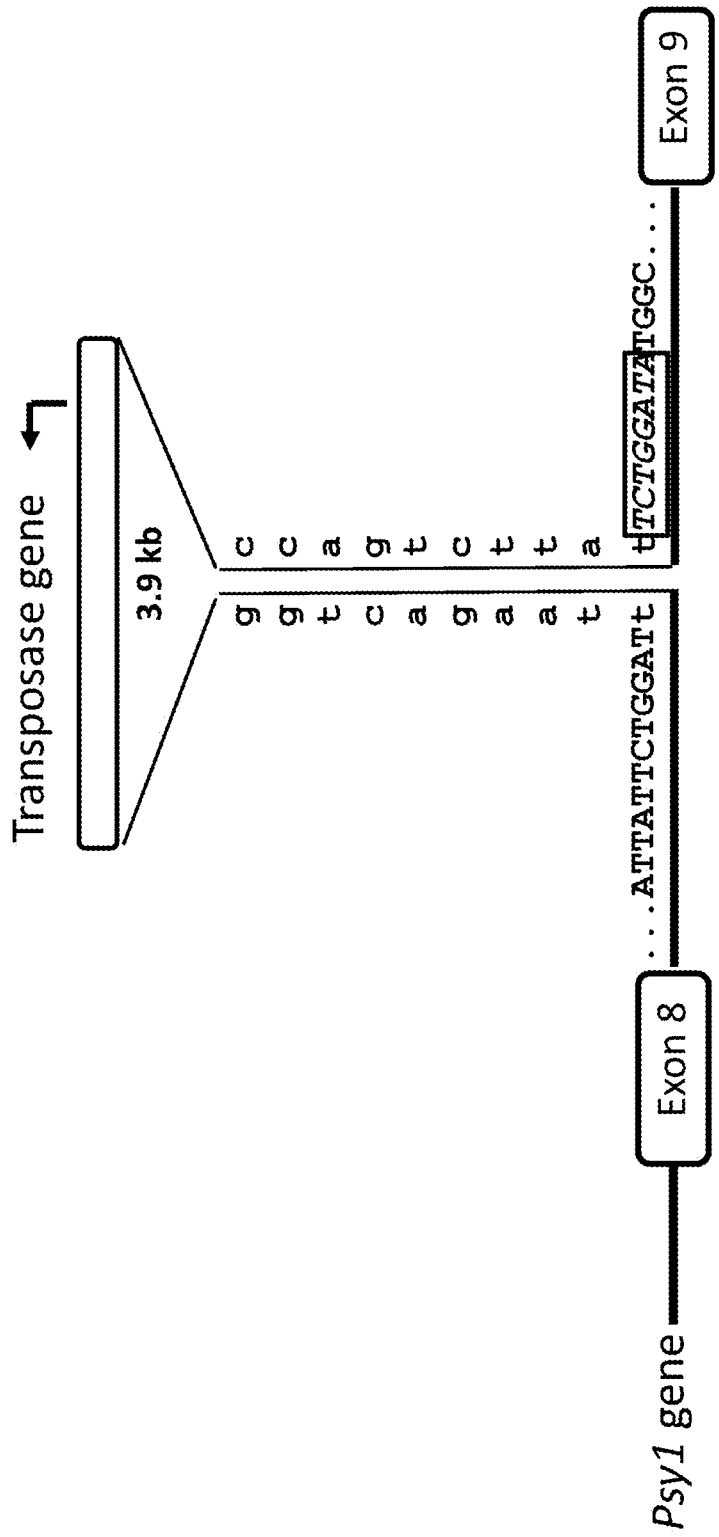

EXON 1 → TCTTGATTTCTTGAAACAAAGTTTGTTTCCCTTCACTTCTTGATATGTAAAGTTGCAATCTTTATAACTTTCTATT
GCTTTGCTAGTAGTGTTTTTGTTATATACAGGGGTGGAGTTAGAGGGTAAGTTACGCATTAGTCGTAACTTTAGTCAA → EXON 2
ACTTCGTAATAATTTAGTAAGTTAAAATATATTAGAGAATTTCAGAATTCATAAACTTTAAATTTTAAATTTTGACT → EXON 3
TCGCTTTGTGTGACTATACAATTACAGATATAAAGTTCAGAGTGGCCATTGTTGAAAGAGAGGGTGGAATTTGTGTAGTTT
TGTTTCCTTTCAGTTGTTTAGTTGAAATATAAAGTTGCAATCTTTAACATTCTTTGTTCACTTTCTATAGTTTGCTAGGTT
CGGTTAAATTCAGTAGCTTAGTTTAGTTTAAACCCTATGCGGAATAGAATGTGTAAAACTTAAACTTCAAATTTTGGCT
CCGCATACGACTAGCGACTATATAATAATAATAATAACTTGTTGACTAAATATAGGAATTGAGCACTTGGCTTCTATGTGTACCAAAA
TTAGAAAATCAGGCGATTATTATAATCTTGTTGACTAAATATAGAATGCATCCATTACCCCAAAAAGTGTGATTCC
ACTGTCATAGGAGAGTTTTTTTTTTTTATTCATTTGCTGATTTTGCTCTAGTTTGGGGTTATAAAGTTCAAATTATTTATCTGGAGG
TTTGTGACACATGGTAGTAATATTGCTAATTTGCTGTAGTTTGCTCTAGTTTGGGGTTATAAAGTTCAAATTATTTATCTGGAGG
GTAGGGGTGGGGGTGTCTATAATGCCAGGTTATGGTTTTACGTGAACCTCACTACTGGTAGTGTGTTTAGATTATCAC
ATCCACTCAGTGTTCCGTGCCGTGTCTAACTGTATCCTTGTTAGTTGCTTTGTTGTTTCCCTCTTTTATACCTATT
ATTATTCGTGTGGCTGTTGTACTCGAACGAGGGTCATCGGGGAACAACCTCTTACCTCCGTGAGGTAGAGCTATGGTCTGTGTC
TTGATATGTTGATTCTACCCTCCCCAGATCCCTCTTGTAGGATTTCACTATATTGTAATATTAACTTGAGGTCACTATAGGAGCTCA
AAACTTCTAATTTTGAAGTCAAGAAACCAGGTTACTCCTGGGTAATTTGTTTGAGTGAGGAAAAGTTGGTTTGCCTTGTCCTGTGGGAATCTACTA
TCTCATTTTGCAGAAGTCAAGAAACCAGGTTACTCCTGGGTAATTTGTTTGAGTGAGGAAAAGTTGGTTTGCCTGTCCTGGGAATCTACTA
TTATAATCTTTTTCTACAGAGGAGAAGAATAAACTAAGTAAGTTTGGAAGTGACAAAAGAAGACAAAAATCTTGGAATTGTTTT
GGAGTAATTTATTTCTATAAACTAAGTAAGTTTGGAAGTGACAAAAGAAGACAAAAATCTTGGAATTGTTTT
AGACAACCAAGGTTTTCTTGCTCAGAATGTCTGTTGCCTTGTGTTTATGGGTTGTTTCTCCCTTGTGACGTCTCAAATGGG → EXON 4
ACAAGTTTCATGATCAGTCCGGGAACAACCGTTTTTTTTTGATTCATCGAGGCATAGGAATTTGGTGTCCAATGA
GAGAATCAATAGAGGTGGTGAAGCAAACTAATAATGGACGGAAATTTCTGTACGGTCTGCTCTATTTTGGCTACTC
CATCTGGAGAACGGACGATGACATCGGAACAGAGATGGTCTATGATGGTTTGAGGCAGGCAGCCTTGGTGAAGAGG
CAACTGAGAATCTACCAATGAGTTAGAACGGGAAGCCGGATATACCTATTCCGGGAATTTGGGCTTGTTGAGTGAAGC
ATATGATAGGTGTGGTGAAGTATGTGCAGAGTGCAAAGACGTTTAACTTAGTTAGCTTCATGTTATTGATGAAGACAAATTTGA → EXON 5
CGTTTACCAAATATTATTTGGTAAGCACTAATTATGAATATATATATGTTCATGTTATTGATGAAGACAAATTTGA → EXON 5
TCTTTGTTTGTTTATTCAGGAACTATGCTAAATGACTCCCGAGAGAAGAAGGGCTATCTGGGCAATATATGTGAGGT
TTCTAGCCATTTAATAACAGTTACCGCCACAAACACATATGATTAATCGGGACGAGAAAAAAGAAATGAAGTTTG
AGTTTTGAGGGTCATATGTAATAGGTAATCCGAGCTTGAGATGTTTATTGTCATATCATGCTCAATA

CACTAACATTACGTCGTCTGTGGATCCTGAAATGGCTTGGATTGCTATTATTCTGGATtaagactggtcaacgac
cggaaccgggtcaccgaccggaatgaaccggtaaccggaccggaatccgttgaccggaatccgttgaccgt
accgggatgaaccggaccggaattaccggatggttcatcgttccgttccgttccactatataccggacgga
ccgaatgaaccggaaccgacccggatggaacggatgaacggattaacggacgatattttttaaattacgaaata
taattttttattttattttaagtataaattaatagttttttaaattatactataattttaacttaagttttatttt
aaagatatttttattactttttttttattattgtttaagtttgcaagtaatctaataaagttttcaaaatttaaatc
ttttgaagtttatactttataagttattacttattattttatttaataatttatttttataagttatatttataacttgt
atcttgtaaatattaaatatttttaaaatttgtaattaaaaagtaaattacaaaaaattaaaaaaatatca
atttaattatttaaatttgtaacaaattacaattcaattttaaactattagtagagtacatagcttacgcagc
caccttctaggaagggttctgtttcaactatgtctcgaattaatactaatatgttgtatagtccgtaaatcctc
tttctaactcagctaggattgattgtgatcaacttctgtcttgtaaagctcgttgacgatctgaattcga
tgccatcgtcactaccacatccaatagttgaatctatgaaaagttcaaattgactatctaactttggaagtcctt
gatttctacgctcagcatttatccaatctctaaataacactgtatctccaggctgtcttctgctaacgaatatc
tgtggtctccaatttgaaatcttgcgcgctgaaagctgcctccgaactactgatgatcctgaattgcaagcac
atccttcaccatcctactaagttttgatattgagctccaacagttctccaccagttcaatagttccggtatacc
attatcgtttgtaatatcatctgtaccctgttcaagatatttaacatattcacattattagaagagtcaagacc ← Transposon
aagtttatgtttcactcgtccatgagcaccacttgatttgtagacgtttgaggatttcaacattatctaagaa
tgaatatttatcatacatttctttcaaagtatttatactattttgacatgttaccaatcaggttcttcttc
aggttgaatatctaaattctgataaatgcattcaactaaagcttttgtaccatatcttttatattcggggttgaa
aagaagtgcagttaaataaatttgaggaataggaaaaaaaatatttttaaattttgtaatcataacttcaatagc
agaggtgaataaagtatttgtttttatattcagaaaaaaatttagtagcatcataaaatgattcaaaaatatctaagttcatt
aatagtaggataatatatcactactactactatcatttaattttaaattcaggataagcattatgattattaataagcgtagtaatagg
tacttcatcccaatcataaattcaagcaacttcaagcatatcataaaaggaattccatctagttttttacatgcttcggaacttt
ttgtctatatgcataagtttaaatgcattacaaagttcttaaattgattaattctactactactattcatatgaaaaat
tctaaacggaagtttaaatgcattacaaagttcttaaattgattaattctactactactattcatatgaaaaat
ataaaacaagcattatcaattatcacaactatttcaaataatttcaaacacgtcactaacaaccaaatttaa
tatatgcgcggcacatctaacatgaaaagcatatttactaataggacaaagtctaggttctagcaaattaatagc
atttaattagcagaggcattatctaaagtaactaacgactttatcacaaagaccaaaaaaatctaaaattc
caacacagtagcaatataaattccgttttttctttttgacaaatttataaccataatctcttttttgtaa
attccaattataatcgatccaatgccgcagtaacagttaaataatcaaaaccattagg FIGURE 8 (Cont. 2)

actacgaccatatcagtagtaatagcaactctacaatccattagttcaaaatagcacgtaaatattgacaatgtt
tttcttgaaattcgaaaatatctcttttaccatgctcttgataaacctgaaaactaggattatatgtttcacga
ataagcaataaaacccgatgttctccaaaactaaaagtaaaccacaaacaacaacaaccattttgcaaagttttc
acgatcacgatccttgttatagttcgatgtgtaagaggaccacttggttcgaagtattttaactcacttgaacca
tattgatcctctaaccgattcttcaacattacaattccaccaacttcaagagaagacatatgcaaaccactct
ttactatgctgttaatcaaatgtttttttaatccccccgttgaacctcccgtcccaccagatgtatattaaaatg
ttgtttacaaagattacatatactaaaagttttttttcttcattcaaataacaaaatttccacacatgtgattttaaag
aacgttgtacctggtcttacctctagttggaataataagggacgagtagttccaaccggagtggagcttcaata
cctatactattgactgtattgagtcggcggcgggctagtcgtcgtgtatcatctaaatctacttcttcatctaaatt
taattgttcatccgttccactctcttcatttcttgattaataacaatatcttcatagagttcatgggagtcg
gactatctgaattaatatttataggacgggacgggaaaaactagttcattcacatgcgtaaattcatctgtattt
atctaacaagagaggaatttagatttagacgaactagcaccctttgttagttttttaactaattttttactgattc
tactagacctttttacttccacttttttttagaagactccatgatataaaattataaattataaaatacgaaactta
acaagaacaacttacaagttaaataattaaaaaataaaattaagattagagagtggaacgaagttaccaaac
gtttgtataagaacaaacgattatatgaaaattaaatattgatgtcgaaatttgaaatgtaatttgaaatatattctct
tccgaaatacaccaaatgattatatttgaagttgtaaatttgtaaataaaatttttttacacacaactctaattatacaaca
aaaaactagccgtttaattttttccgtttgggtgggggggctgcactgcagtcgagctgcagtgcttatgcagactgc
agtctgcagtcgcgagggcggattttgaaaaaaattaataatatatattaaataaaccggaaccggaacggaaccgaccg
gaaccggaatgaaccggatgaaccggtacccgtacccggcaaccgaaacggaacggaacggaacggtaccggaacggt
tttagaatatccggccccgttccgttgccagtgctta<mark>TCTGGATA</mark>TGGCAAAACCATTTTATTAGTACTAGATATCGAATA
ACTACACATTTGACCCTACTATTCTGGCAAATAACCTCACTCGTTACTCGGTGTTTTCCAGTATGGGCATCTTTGGTCT
ATCACCCTTGTCTACTATTCTGGCAAATAACCTCACTCGTTACTCGGTGTTTTCCAGTATGGGCATCTTTGGTCT
TGTACCGCAAAATACTAGATGAGATTGAAGCCAATGACTACAACAACTTCACAAGAGAGCATATGTGAGCAAATCA
AAGAAGTTGATTGCATTACCTATTGCATATGCATATGCAAAATCTCTTGTGCCTCCTACAAAACTGCCTCTCTTCAAGATA
AAGCATGAAATGAAGAGATATATATATATATATAGCAATATACATTAGAAGAAAAAAGGAAGAAGAAATGTTGT
TGTATTGATATAAATGTATATCATAAATATTAGGTTGTAGTAACATTCAATATAATTATCTCTTGTAGTTGTTGTAT
CTTCACTTTATCTCAACTCCTTTGAGAGAACTTTCCGTAGTTATCGCTTTGCACTTGGTTACTCAGAATTTTACTG
TGGGCATGATAATTGATATACCAAATTCAGTTTTGATTCTTGCTATCGAAAAATTTGTTATTACATTTTTTGGGGGAAA
GGAA ⬅ Transposon (Cont.)

⬅ EXON 9

FIGURE 8 (Cont. 3)

SEQUENCE LISTING

```
<160> NUMBER OF SEQ ID NOS: 29

<210> SEQ ID NO 1
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 1 atctggata                                                                9

<210> SEQ ID NO 2
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 2 tctggata                                                                 8

<210> SEQ ID NO 3
<211> LENGTH: 3903
<212> TYPE: DNA
<213> ORGANISM: Lycopersicon

<400> SEQUENCE: 3
ttaagactgg tcaacggacc ggaacgggt caccggaccg gaatgaaccg gtaccggacc          60
ggaccggaat ccgttgaccg gaattttgac cggtaccggg atgaaccgga ccggaattac        120
cgggatggtt catcggttcc gtcccgttcc actatatacc gggacggaac cggaatgaac        180
cggaacggac cgggatggaa cgggacggga ttaacgggac gatattttt aaattacgaa         240 aatataattt tttttatttt ttaagtataa attaatagtt tttaaattta tactataatt        300
tttaacttaa gtttatttta aagatatttt attaatttt ttttattatt gttaagtttg         360
caagtaatct aataaagttt tcaaaattta aatcttttga agtttatact ttataagtta        420
ttacttatat ttattaatat ttatttata agttatattt ataacttgta tcttgtaaat        480
attaaataaa taaaatttgt aatttaaaaa aagtaaatta aattacaaaa attaaaaaat       540
atcaatttaa tttatttaaa tttgtaacaa attacaattt caatttacaa ctattagtag       600
```

```
agtacatagc ttacgcagcc accttctagg aagggttctg tttcaactat gtctcgaatg      660
taatactaat agttgtatag tcccgtaaat cctctttcta actcagctag ggattgattg      720
tgatcaactt ctggtcttgg taaagctcgt tgacgatctt gaatttcgat gccatcgtca      780
ctaccacatc caatagttga atctatgaaa agttcaaatt gactatctaa ctttggaagt      840
ccttgatttc tacgctcagc atttatccaa tctctaaata acactgatat ctccaggctg      900
tcttctgcta acgaatatct gtggtctcca atttgaaatc ttgccgcgct gaaagctgcc      960
tccgaactac tgatgatcct tgaattgcaa gcacatcctt caccatccta ctaagttttg     1020
gatattgagc tccacgattt ctccaccagt tcaatagttc cggtatacca ttatcgtttg     1080
taatatcatc tgtaccctgt tcaagatatt taacaaattc acatttatta gaagagtcaa     1140
gaccaagttt atgtttcact cgtccatgag cacctacttg atttgtagac gtttgaggat     1200
tttcaacatt atctaagaat gaatatttat catacatttc ttttgcaaag tattttatac     1260
tattttgaca tgttaccaaa tcaggttctt cttcaggttg aatatctaaa ttctgataaa     1320
tgcattcaac taaagctttt gtaccatatt ctttatattc ggggttgaaa agaagtgcag     1380
ttaaataaat ttgaggaata ggaaaaaaat atttttttaaa ttttgtaatc ataacttcaa     1440
tagcagaggt gaataaagta tttgttttat attcagaaaa aatagatgaa atctcacata     1500
tgtgtattaa aatttcagaa atagtaggat aatatattcc agaaaaaatt ttagtagcat     1560
cataaaatga tttcaaaaat attctaagtt catttacttc atcccaatca ctatcattaa     1620
ttttaaattc aggataagca ttatgattat taaatagcgt agtaataggt tgtctatatg     1680
cataagcaac ttcaagcata tcataaaagg aattccatct agttttttaca tgcttcggaa     1740 cttttctaaa cggaagttta aatgcattac aaagttcttt aaattgatta attctactac     1800
tactattcat atgaaaaata taaaaacaag cattatcaat tttatcacaa ctattttcaa     1860
ataatttcac accgtcacta acaaccaaat ttaatatatg cgcggcacat ctaacatgaa     1920
aagcatattt actaatagga caaagtctag gttctagcaa attaatagca tttaaattag     1980
cagaggcatt atctaaagta atactaacga ctttatcaca aagaccaaaa aaatctaaaa     2040
tttccaacac agtagtagca atataaattc cggttttttt cttttgacaa atttttataac     2100 caataattct ttttttgtaaa ttccaattat aatcgatcca atgcgcagta acagttaaat     2160
aatcaaaacc attaggacta cgacccatat cagtagtaat agcaactcta caatccatta     2220
gttcaaaata ggcacgtaaa tattgacaat gttttttcttg aaattcgaaa atatctcttt     2280
ttaccatgct tcttgataaa ccttgaaaac taggattata tgtttcacga atataagcaa     2340
taaaacccgg atgttctcca aaactaaaag gtaaaccaca acaacaacc ttttttgcaa     2400 agttttcacg atcacgatcc ttgttatagg ttcgatgtgt aagaggacca cttgggttcg     2460
aagtatttaa ctcactttga accatatttg atcctctaac cgattcttca acattacaat     2520
ttccaccaac ttcaagagaa gacatatatg caaaccactc tttactatgc ttgttaatca     2580
aatgtttttt taatcccccc gttgaacctc ccgtcccacc agatgtatat ttaaaatgtt     2640
gtttacaaag attacatata ctaaaagttt ttcttcatt caaataacaa aatttccaca     2700 catgtgatttt taaagaacgt tgtaccttgg tcttacctct agttggaata ataagggggac     2760 gagtagttcc aaccggaggt ggagcttcaa tacctatact attgactgta ttgaggtcgg     2820
cggcggggct agtcggtgta tcatctaaat ctacttcttc atctaaattt aattgttcat     2880
ccgtttccac ttcttcattt tcttgattaa taccataata tctttcatag agttcatggg     2940
gagtcggact atctgaatta atatttatag gaccgggacg ggaaaaaacta gtttcattca     3000
```

```
catgcgtaaa ttcatctgta tttattctaa caagaggaat tttagattta gacgaactag    3060
cacctttgtt agtttttta actaattttt ttactgattc tactagacct tttttacttc    3120 cactttttt agaagactcc atgatataaa attataaatt ataaaatacg aaacttaaca    3180
agaacaactt acaagttaaa taataaatta aaaaaataaa tataagatta gagagtggaa    3240
cgaagttacc aaacgtttgt ataagaacaa acgattataa tgaaaattaa aatattgatg    3300
tcgaaacttg aaatttgaag aagattcctc ctccgaaata caccaaatga ccaaatgata    3360
taagttatac ttataaatat gaatgtaatt tggaaatata tattctctga aatactcaga    3420
ttatatttgt aagttgtaaa cttgtaaata aaatttttt acacacaact ctaatttata    3480
caacaaaaaa actagccgtt ttaattttc cgtttggggt ggggggggct gcactgcagc    3540
tgcagtgctt tatgcagact gcagtctgca gtctgcaggg gcgggatttt tgaaaaaaat    3600
ttaaatttta aaatataatt tataaaaaat ataaatataa attatataaa atataaaata    3660
taaaaaaatt aatatatatt aaataaaccg gaccggaacc ggaacggacc ggaccggaac    3720
cggaatgaac cgggatgaac cggtaccggt acaccggtac gaaactacgg ttccgtcccg    3780
ttccgtgtac cggtttagaa tatcccggcc cgtcccgtag gcaaccgaaa cgggacgaac    3840
cggaacgaac cggaacggta ccggaacggt accggtacgt cccgttccgt tgcccagtct    3900
tat                                                                 3903

<210> SEQ ID NO 4
<211> LENGTH: 3911
<212> TYPE: DNA
<213> ORGANISM: Artificial Sequence
<220> FEATURE:
<223> OTHER INFORMATION: Synthetic polynucleotide

<400> SEQUENCE: 4
ttaagactgg tcaacggacc ggaaccgggt caccggaccg gaatgaaccg gtaccggacc      60
ggaccggaat ccgttgaccg gaattttgac cggtaccggg atgaaccgga ccggaattac     120
cgggatggtt catcggttcc gtcccgttcc actatatacc gggacggaac cggaatgaac     180
cggaacggac cgggatggaa cgggacggga ttaacgggac gatattttt aaattacgaa     240 aatataattt ttttattttt ttaagtataa attaatagtt tttaaattta tactataatt     300
tttaacttaa gtttatttta aagatatttt attaattttt ttttattatt gttaagtttg     360
caagtaatct aataaagttt tcaaaattta aatcttttga gtttatact ttataagtta     420 ttacttatat ttattaatat ttattttata agttatattt ataacttgta tcttgtaaat     480
attaaataaa taaaatttgt aatttaaaaa aagtaaatta aattacaaaa attaaaaaat     540
atcaatttaa tttatttaaa tttgtaacaa attacaattt caatttacaa ctattagtag     600
agtacatagc ttacgcagcc accttctagg aagggttctg tttcaactat gtctcgaatg     660
taatactaat agttgtatag tcccgtaaat cctctttcta actcagctag ggattgattg     720
tgatcaactt ctggtcttgg taaagctcgt tgacgatctt gaatttcgat gccatcgtca     780
ctaccacatc caatagttga atctatgaaa agttcaaatt gactatctaa ctttggaagt     840
ccttgatttc tacgctcagc atttatccaa tctctaaata acactgatat ctccaggctg     900
tcttctgcta acgaatatct gtggtctcca atttgaaatc ttgccgcgct gaaagctgcc     960
tccgaactac tgatgatcct tgaattgcaa gcacatcctt caccatccta ctaagttttg    1020
gatattgagc tccacgattt ctccaccagt tcaatagttc cggtataccca ttatcgtttg    1080
```

-continued

```
taatatcatc tgtaccctgt tcaagatatt taacaaattc acatttatta gaagagtcaa    1140
gaccaagttt atgtttcact cgtccatgag cacctacttg atttgtagac gtttgaggat    1200
tttcaacatt atctaagaat gaatatttat catacatttc ttttgcaaag tattttatac    1260
tattttgaca tgttaccaaa tcaggttctt cttcaggttg aatatctaaa ttctgataaa    1320
tgcattcaac taaagctttt gtaccatatt ctttatattc ggggttgaaa agaagtgcag    1380
ttaaataaat ttgaggaata ggaaaaaaat atttttttaaa ttttgtaatc ataacttcaa    1440
tagcagaggt gaataaagta tttgttttat attcagaaaa aatagatgaa atctcacata    1500
tgtgtattaa aatttcagaa atagtaggat aatatattcc agaaaaaatt ttagtagcat    1560
cataaaatga tttcaaaaat attctaagtt catttacttc atcccaatca ctatcattaa    1620
ttttaaattc aggataagca ttatgattat taaatagcgt agtaataggt tgtctatatg    1680
cataagcaac ttcaagcata tcataaaagg aattccatct agttttttaca tgcttcggaa    1740 cttttctaaa cggaagttta aatgcattac aaagttcttt aaattgatta attctactac    1800
tactattcat atgaaaaata taaaacaag cattatcaat tttatcacaa ctattttcaa    1860
ataatttcac accgtcacta acaaccaaat ttaatatatg cgcggcacat ctaacatgaa    1920
aagcatattt actaatagga caaagtctag gttctagcaa attaatagca tttaaattag    1980
cagaggcatt atctaaagta atactaacga ctttatcaca aagaccaaaa aaatctaaaa    2040
tttccaacac agtagtagca atataaattc cggttttttt cttttgacaa atttttataac    2100 caataattct tttttgtaaa ttccaattat aatcgatcca atgcgcagta acagttaaat    2160
aatcaaaacc attaggacta cgacccatat cagtagtaat agcaactcta caatccatta    2220
gttcaaaata ggcacgtaaa tattgacaat gttttttcttg aaattcgaaa atatctcttt    2280
ttaccatgct tcttgataaa ccttgaaaac taggattata tgtttcacga atataagcaa    2340
taaaacccgg atgttctcca aaactaaaag gtaaaccaca acaacaacc attttttgcaa    2400 agttttcacg atcacgatcc ttgttatagg ttcgatgtgt aagaggacca cttgggttcg    2460
aagtatttaa ctcactttga accatatttg atcctctaac cgattcttca acattacaat    2520
ttccaccaac ttcaagagaa gacatatatg caaaccactc tttactatgc ttgttaatca    2580 aatgttttt taatcccccc gttgaacctc ccgtcccacc agatgtatat ttaaaatgtt    2640
gtttacaaag attacatata ctaaaagttt tttcttcatt caaataacaa aatttccaca    2700
catgtgattt taaagaacgt tgtaccttgg tcttacctct agttggaata ataaggggac    2760
gagtagttcc aaccggaggt ggagcttcaa tacctatact attgactgta ttgaggtcgg    2820
cggcggggct agtcggtgta tcatctaaat ctacttcttc atctaaattt aattgttcat    2880
ccgtttccac ttcttcattt tcttgattaa taccataata tctttcatag agttcatggg    2940
gagtcggact atctgaatta atatttatag gaccgggacg ggaaaaacta gtttcattca    3000
catgcgtaaa ttcatctgta tttattctaa caagaggaat tttagattta gacgaactag    3060
cacctttgtt agttttttta actaatttt ttactgattc tactagacct ttttacttc    3120 cactttttt agaagactcc atgatataaa attataaatt ataaaatacg aacttaaca    3180 agaacaactt acaagttaaa taataaatta aaaaaataaa tataagatta gagagtggaa    3240
cgaagttacc aaacgtttgt ataagaacaa acgattataa tgaaaattaa aatattgatg    3300
tcgaaacttg aaatttgaag aagattcctc ctccgaaata caccaaatga ccaaatgata    3360 taagtttatac ttataaatat gaatgtaatt tggaaatata tattctctga aatactcaga    3420
ttatatttgt aagttgtaaa cttgtaaata aaatttttttt acacacaact ctaatttata    3480
```

| | |
|---|---:|
| caacaaaaaa actagccgtt ttaatttttc cgtttggggt ggggggggct gcactgcagc | 3540 |
| tgcagtgctt tatgcagact gcagtctgca gtctgcaggg gcgggatttt tgaaaaaaat | 3600 |
| ttaaatttta aaatataatt tataaaaaat ataaatataa attatataaa atataaaata | 3660 |
| taaaaaaatt aatatatatt aaataaaccg gaccggaacc ggaacggacc ggaccggaac | 3720 |
| cggaatgaac cgggatgaac cggtaccggt acaccggtac gaaactacgg ttccgtcccg | 3780 |
| ttccgtgtac cggtttagaa tatcccggcc cgtcccgtag gcaaccgaaa cgggacgaac | 3840 |
| cggaacgaac cggaacggta ccggaacggt accggtacgt cccgttccgt tgcccagtct | 3900 |
| tattctggat a | 3911 |

<210> SEQ ID NO 5
<211> LENGTH: 9012
<212> TYPE: DNA
<213> ORGANISM: Artificial Sequence
<220> FEATURE:
<223> OTHER INFORMATION: Synthetic polynucleotide

<400> SEQUENCE: 5

| | |
|---|---:|
| tcttgatttc ttgaaacaaa ggtttgtttc ccttcacttc ttgatatgta aagttgcaat | 60 |
| ctttataact ttctattgct ttgctagtgt ttttgttata tacaggpggt ggagttagag | 120 |
| ggtaagttac gcatttagtc gtaactttag tcaaacttcg taataattta gtaagttaaa | 180 |
| atatattaga aattttcaga attcataaac tttaaatttt aaattttgac ttcgctttgt | 240 |
| gtgactatac aattacagaa attcagagtg gccattgttg aaagagaggg tggaatttgt | 300 |
| gtaagtttg tttcctttca gttcttgata tataaagttg caatctttaa cattctttgt | 360 |
| tcactttcta taggtttgct aggttcggtt aaattcagta gctttagttt aaaccctatg | 420 |
| cggaatagag aatgtgtaaa ctttaaactt caaattttgg ctccgcatac gactagcgac | 480 |
| tatataataa taggaattga gcacttggct tttgtatata gcttctatgt gtaccaaaat | 540 |
| tagaaaatca ggcgattatt ataatcttgt tgactaaata tagaatgcat ccattacccc | 600 |
| caaaaagtgt gattccactg tcataggagg ttttttttat ttcattttat ttgtgctttc | 660 |
| aataatgtag agtagtttta caaagatcct ttctttgtga cacatggtag taatattgct | 720 |
| gattttgctg tagttttggg gttataaagt tcaaattatt tatctggagg gtaggggtg | 780 |
| ggggtgtcta taatgccagg ttatggtttt acgtgaacct caataaatta ttggtagaat | 840 |
| ctaagaaatc cactcagtgt tccgtgcggt ggtcttgctt ttgatttcag catcactggt | 900 |
| agttgattgt gtttagatta tcacattatt ctgtggctgt aactgtatcc ttgttagttg | 960 |
| ctttgtttct acactgttgt tttccctctt ttatacctat tttgatatgt tgtactcgaa | 1020 |
| cgagggtcat cggggaacaa cctctttacc tccgtgaggt agagctatgg tctgtgtcca | 1080 |
| ctctacccctc cccagatccc tcttgtagga tttcactata ttgtaatatt aacttgaggt | 1140 |
| cactatagga gctcaaaaac ttctaatttt gaatcaatgt ctggttatac ttttttttgtc | 1200 |
| ataactgtat ctcaaatgtg gtgtttggtt tatctcattt tgcagaagtc aagaaacagg | 1260 |
| ttactcctgt ttgagtgagg aaagttggt tgcctgtct gtggtctttt tataatcttt | 1320 |
| ttctacagaa gagaaagtgg gtaattttgt ttgagagtgt aaatattctc tagtgggaat | 1380 |
| ctactaggag taatttattt tctataaact aagtaaagtt tggaaggtga caaaaagaaa | 1440 |
| gacaaaaatc ttggaattgt tttagacaac caaggttttc ttgctcagaa tgtctgttgc | 1500 |
| cttgttatgg gttgtttctc cttgtgacgt ctcaaatggg acaagtttca tggaatcagt | 1560 |

```
ccgggaggga aaccgttttt tgattcatc gaggcatagg aatttggtgt ccaatgagag    1620
aatcaataga ggtggtggaa agcaaactaa taatggacgg aaattttctg tacggtctgc    1680
tattttggct actccatctg gagaacggac gatgacatcg aacagatgg  tctatgatgt    1740 ggttttgagg caggcagcct tggtgaagag gcaactgaga tctaccaatg agttagaagt    1800
gaagccggat atacctattc cggggaattt gggcttgttg agtgaagcat atgataggtg    1860
tggtgaagta tgtgcagagt atgcaaagac gtttaactta ggttagcttc ttcaatctat    1920
tcattcgttt accaaatatt atttggtaag cactaattat gaatatatat atgttcatgt    1980
tattgatgaa gacaaaattt gatctttgtt tgtttattca ggaactatgc taatgactcc    2040
cgagagaaga agggctatct gggcaatata tggtgaggtt tctagccatt taataacagt    2100
tacgcgcaca aacacatatg attaatcggg gacgagaaaa aaagaaatga agtttgagtt    2160
ttgagggtca tatgtaatag gtaaatccga gcttgactag cttgagatgt ttattgtcat    2220
atcatgctca atactaacca aaacactgaa aaagaacttg attatattta catactaata    2280
ttttcatttg cgttgctgtt cacattttta cctatggaac tggttttttgt gatttgttat    2340 acttcatatt cgatgttaat aaaatatatc attcctccct ttttctccac ttcaagcttt    2400
actgtagtgt tgaaagggga aactccttt  aatgattgca tatataaacg aacttcttga    2460
gttgaatagt ttctcattat gatctgttta aacagtatgg tgcagaagaa cagatgaact    2520
tgttgatggc ccaaacgcat catatattac cccggcagcc ttagataggt gggaaaatag    2580
gctagaagat gttttcaatg gcggccatt  tgacatgctc gatggtgctt tgtccgatac    2640 agttctaac  tttccagttg atattcaggt tagtctacca attctatggt ctttatattt    2700
gttcaatttg cgtttgatgt cactttttgct gagggctttt ctaatagctt acttcagcct    2760
agcggaaatg tttgtagttg aatctctagt tctgtctcct atatctgttt ctctcgtcct    2820
agatactaca catacttcat ttctgtttta acattttatt cgtctttttgg tgttgttttg    2880 tatgtgaatc atatatttgg aacagaatca ttattagttc acatgatttc atttgctttc    2940
ttcaatagcg taattgtcta accttccaat atatgttgca gccattcaga gatatgattg    3000
aaggaatgcg tatggacttg agaaaatcga gatacaaaaa cttcgacgaa ctataccttt    3060
attgttatta tgttgctggt acggttgggt tgatgagtgt tccaattatg ggtatcgccc    3120
ctgaatcaaa ggcaacaaca gagagcgtat ataatgctgc tttggctctg gggatcgcaa    3180
atcaattaac taacatactc agagatgttg gagaagagta agtacaaagc tgtgttttac    3240
gcacataatt ttttttgcta atatttacat atcaaaatat aggaaaatga gctcttcggt    3300
tatccggttt atatttttt  tatgtcaaca taatagtata aagtaattag tatcagtcgt    3360
tctgggaata aaattgcaga actcaattta gccgtgttgt gaaatcctgc ttgttttgag    3420
agcttaaagc tcattagtta gtcgttagag acgaagaaat tcttcgttgt ccatctttat    3480
tccaccttaa agttgtgata ttttcattat tggtacattt ggcaaaaaca cctgaacaaa    3540
tttatgacgg atgcctttgt gaagtcacta tacctgtcta gtcggcgttt atcacatttc    3600
tttgacatat tgaactttga aacatgatat cagctctaga cagtgacgag ccatgatcaa    3660 tttcttcct  ttattctttc tttggaagtg ccgtatttag gcttccgttg ttcttatata    3720
ttgctttccc tgcagtgcca gaagaggaag agtctacttg cctcaagatg aattagcaca    3780
ggcaggtcta tccgatgaag atatatttgc tggaagggtg accgataaat ggagaatctt    3840
tatgaagaaa caaatacata gggcaagaaa gttctttgat gaggcagaga aaggcgtgac    3900
agaattgagc tcagctagta gattcccctgt aagcattcgt aaactcttta gttttatgaa    3960
```

```
atgattcttt tttcgcgtta ttagatgaat atggttgctt gtgttgagta tttctaggtc    4020
gatgaagttg agacaagggt ttttaagttt taacgacttt tacggggtgc catgttatct    4080
gctacctaat cttaggtagt tgaccggaag ggctagaatt ttaacctcat gttcaccta     4140 ccaaccaaga aatgaacctc gcatagagct cgtagttatg aatatttgct ttggcatgac    4200
attgtgcgga tcatgaaatg tcttagatta tatggaaaaa tcattctatt acatcgaata    4260
gatacattag atctaagaag cacgccgtgt tgtaaatgag aaattctata gctcagatct    4320
ttagttttct ctgaacgacc tacaaaccaa cggataacct tgtattgagc ttgtcgttct    4380
cagtatttgc actaacatta cgtcgtgtgg atcctgaaat ggcttggatt gctattattc    4440
tggatttaag actggtcaac ggaccggaac cgggtcaccg gaccggaatg aaccggtacc    4500
ggaccggacc ggaatccgtt gaccggaatt ttgaccggta ccgggatgaa ccggaccgga    4560
attaccggga tggttcatcg gttccgtccc gttccactat ataccgggac ggaaccggaa    4620
tgaaccggaa cggaccggga tggaacggga cgggattaac gggacgatat tttttaaatt    4680
acgaaaatat aatttttttt attttttaag tataaattaa tagttttaa atttatacta     4740 taatttttaa cttaagttta ttttaaagat attttattaa ttttttttta ttattgttaa    4800
gtttgcaagt aatctaataa agttttcaaa atttaaatct tttgaagttt atctttata    4860 agttattact tatatttatt aatatttatt ttataagtta tatttataac ttgtatcttg    4920
taaatattaa ataaataaaa tttgtaattt aaaaaaagta aattaaatta caaaaattaa    4980
aaaatatcaa tttaatttat ttaaatttgt aacaaattac aatttcaatt tacaactatt    5040
agtagagtac atagcttacg cagccacctt ctaggaaggg ttctgtttca actatgtctc    5100
gaatgtaata ctaatagttg tatagtcccg taaatcctct ttctaactca gctagggatt    5160
gattgtgatc aacttctggt cttggtaaag ctcgttgacg atcttgaatt tcgatgccat    5220
cgtcactacc acatccaata gttgaatcta tgaaaagttc aaattgacta tctaactttg    5280
gaagtccttg atttctacgc tcagcattta tccaatctct aaataacact gatatctcca    5340
ggctgtcttc tgctaacgaa tatctgtggt ctccaatttg aaatcttgcc gcgctgaaag    5400
ctgcctccga actactgatg atccttgaat tgcaagcaca tccttcacca tcctactaag    5460
ttttggatat tgagctccac gatttctcca ccagttcaat agttccggta taccattatc    5520
gtttgtaata tcatctgtac cctgttcaag atatttaaca aattcacatt tattagaaga    5580
gtcaagacca agtttatgtt tcactcgtcc atgagcacct acttgatttg tagacgtttg    5640
aggattttca acattatcta agaatgaata tttatcatac atttcttttg caaagtattt    5700
tatactattt tgacatgtta ccaaatcagg ttcttcttca ggttgaatat ctaaattctg    5760
ataaatgcat tcaactaaag cttttgtacc atattcttta tattcggggt tgaaaagaag    5820
tgcagttaaa taaatttgag gaataggaaa aaaatatttt ttaaattttg taatcataac    5880
ttcaatagca gaggtgaata aagtatttgt tttatattca gaaaaaatag atgaaatctc    5940
acatatgtgt attaaaattt cagaaatagt aggataatat attccagaaa aaattttagt    6000
agcatcataa aatgatttca aaaatattct aagttcattt acttcatccc aatcactatc    6060
attaatttta aattcaggat aagcattatg attattaaat agcgtagtaa taggttgtct    6120
atatgcataa gcaacttcaa gcatatcata aaaggaattc catctagttt ttacatgctt    6180
cggaactttt ctaaacggaa gtttaaatgc attacaaagt tctttaaatt gattaattct    6240
actactacta ttcatatgaa aaatataaaa acaagcatta tcaattttat cacaactatt    6300
```

```
ttcaaataat ttcacaccgt cactaacaac caaatttaat atatgcgcgg cacatctaac    6360
atgaaaagca tatttactaa taggacaaag tctaggttct agcaaattaa tagcatttaa    6420
attagcagag gcattatcta aagtaatact aacgactttta tcacaaagac caaaaaaatc   6480
taaaatttcc aacacagtag tagcaatata aattccggtt ttttttcttt gacaaatttt    6540
ataaccaata attcttttttt gtaaattcca attataatcg atccaatgcg cagtaacagt   6600
taaataatca aaaccattag gactacgacc catatcagta gtaatagcaa ctctacaatc    6660
cattagttca aaataggcac gtaaatattg acaatgtttt tcttgaaatt cgaaaatatc    6720 tcttttttacc atgcttcttg ataaaccttg aaaactagga ttatatgttt cacgaatata   6780
agcaataaaa cccggatgtt ctccaaaact aaaaggtaaa ccacaaacaa caaccatttt    6840
tgcaaagttt tcacgatcac gatccttgtt ataggttcga tgtgtaagag gaccacttgg    6900
gttcgaagta tttaactcac tttgaaccat atttgatcct ctaaccgatt cttcaacatt    6960
acaatttcca ccaacttcaa gagaagacat atatgcaaac cactctttac tatgcttgtt    7020
aatcaaatgt ttttttaatc cccccgttga acctcccgtc ccaccagatg tatatttaaa    7080
atgttgttta caaagattac atatactaaa agttttttct tcattcaaat aacaaaattt    7140
ccacacatgt gattttaaag aacgttgtac cttggtctta cctctagttg gaataataag    7200
gggacgagta gttccaaccg gaggtggagc ttcaatacct atactattga ctgtattgag    7260
gtcggcggcg gggctagtcg gtgtatcatc taaatctact tcttcatcta aatttaattg    7320
ttcatccgtt tccacttctt cattttcttg attaatacca taatatcttt catagagttc    7380
atggggagtc ggactatctg aattaatatt tataggaccg ggacgggaaa aactagtttc    7440
attcacatgc gtaaattcat ctgtatttat tctaacaaga ggaattttag atttagacga    7500 actagcaccct ttgttagttt ttttaactaa ttttttttact gattctacta gaccttttttt  7560 acttccactt tttttagaag actccatgat ataaaattat aaattataaa atacgaaact    7620
taacaagaac aacttacaag ttaaataata aattaaaaaa ataaatataa gattagagag    7680
tggaacgaag ttaccaaacg tttgtataag aacaaacgat tataatgaaa attaaaatat    7740
tgatgtcgaa acttgaaatt tgaagaagat tcctcctccg aaatacacca aatgaccaaa    7800
tgatataagt tatacttata aatatgaatg taatttggaa atatatattc tctgaaatac    7860
tcagattata tttgtaagtt gtaaacttgt aaataaaatt ttttttacaca caactctaat   7920 ttatacaaca aaaaaactag ccgttttaat ttttccgttt ggggtggggg gggctgcact    7980
gcagctgcag tgctttatgc agactgcagt ctgcagtctg caggggcggg atttttgaaa    8040
aaaatttaaa ttttaaaata taatttataa aaaatataaa tataaattat ataaaatata    8100
aaatataaaa aaattaatat atattaaata aaccggaccg gaaccggaac ggaccggacc    8160
ggaaccggaa tgaaccggga tgaaccggta ccggtacacc ggtacgaaac tacggttccg    8220
tcccgttccg tgtaccggtt tagaatatcc cggcccgtcc cgtaggcaac cgaaacggga    8280
cgaaccggaa cgaaccggaa cggtaccgga acggtaccgg tacgtcccgt tccgttgccc    8340
agtcttattc tggatatggc aaaaccatt tattagtact agatatcgaa taactacatt     8400 tgacccctaca agtaccctgg gttggagtta caatatccca tacctcgtat ctttagtgtt   8460
ctcttattta tcacctttgt ctactattct ggcaaaataa cctcactcgt tactcggtgt    8520
tttccaggta tgggcatctt tggtcttgta ccgcaaaata ctagatgaga ttgaagccaa    8580
tgactacaac aacttcacaa agagagcata tgtgagcaaa tcaaagaagt tgattgcatt    8640
acctattgca tatgcaaaat ctcttgtgcc tcctacaaaa actgcctctc ttcaaagata    8700
```
aagcatgaaa tgaagatata tatatatata tatatagcaa tatacattag aagaaaaaaa    8760
ggaagaagaa atgttgttgt attgatataa atgtatatca taaatattag gttgtagtaa    8820
cattcaatat aattatctct tgtagttgtt gtatcttcac tttatctcaa ctcctttgag    8880
agaactttcc gtagttatct gctttgcact tggttactca gaattttact gtgggcatga    8940
taattgatat accaaattca gttttgattc tatcgaaaaa tttgttatta catttttttg    9000
gggggaaagg aa                                                        9012

<210> SEQ ID NO 6
<211> LENGTH: 5102
<212> TYPE: DNA
<213> ORGANISM: Solanum lycopersicum

<400> SEQUENCE: 6
tcttgatttc ttgaaacaaa ggtttgtttc ccttcacttc ttgatatgta aagttgcaat      60
ctttataact ttctattgct ttgctagtgt ttttgttata tacaggggt ggagttagag      120 ggtaagttac gcatttagtc gtaactttag tcaaacttcg taataattta gtaagttaaa     180
atatattaga aattttcaga attcataaac tttaaatttt aaattttgac ttcgctttgt     240
gtgactatac aattacagaa attcagagtg gccattgttg aaagagaggg tggaatttgt     300
gtaagttttg tttcctttca gttcttgata tataaagttg caatctttaa cattctttgt    360
tcactttcta taggtttgct aggttcggtt aaattcagta gctttagttt aaaccctatg     420
cggaatagag aatgtgtaaa ctttaaactt caaattttgg ctccgcatac gactagcgac     480
tatataataa taggaattga gcacttggct tttgtatata gcttctatgt gtaccaaaat     540
tagaaaatca ggcgattatt ataatcttgt tgactaaata tagaatgcat ccattacccc     600
caaaaagtgt gattccactg tcataggagg ttttttttat ttcattttat ttgtgctttc     660
aataatgtag agtagtttta caaagatcct ttctttgtga cacatggtag taatattgct     720
gattttgctg tagttttggg gttataaagt tcaaattatt tatctggagg gtaggggtg     780 ggggtgtcta taatgccagg ttatggtttt acgtgaacct caataaatta ttggtagaat     840
ctaagaaatc cactcagtgt tccgtgcggt ggtcttgctt ttgatttcag catcactggt    900
agttgattgt gtttagatta tcacattatt ctgtggctgt aactgtatcc ttgttagttg     960 ctttgttct acactgttgt tttccctctt ttatacctat tttgatatgt tgtactcgaa    1020
cgagggtcat cggggaacaa cctctttacc tccgtgaggt agagctatgg tctgtgtcca    1080 ctctacccctc cccagatccc tcttgtagga tttcactata ttgtaatatt aacttgaggt    1140
cactatagga gctcaaaaac ttctaatttt gaatcaatgt ctggttatac tttttttgtc    1200
ataactgtat ctcaaatgtg gtgtttggtt tatctcattt tgcagaagtc aagaaacagg    1260
ttactcctgt ttgagtgagg aaaagttggt ttgcctgtct gtggtctttt tataatcttt    1320
ttctacagaa gagaaagtgg gtaattttgt ttgagagtgg aaatattctc tagtgggaat    1380
ctactaggag taatttattt tctataaact aagtaaagtt tggaaggtga caaaaagaaa    1440
gacaaaaatc ttggaattgt tttagacaac caaggttttc ttgctcagaa tgtctgttgc    1500
cttgttatgg gttgttctc cttgtgacgt ctcaaatggg acaagtttca tggaatcagt    1560
ccgggaggga aaccgttttt ttgattcatc gaggcatagg aatttggtgt ccaatgagag    1620
aatcaataga ggtggtggaa agcaaactaa taatggacgg aaattttctg tacggtctgc    1680
tattttggct actccatctg gagaacggac gatgacatcg gaacagatgg tctatgatgt    1740

-continued

```
ggttttgagg caggcagcct tggtgaagag gcaactgaga tctaccaatg agttagaagt      1800
gaagccggat atacctattc cggggaattt gggcttgttg agtgaagcat atgataggtg      1860
tggtgaagta tgtgcagagt atgcaaagac gtttaactta ggttagcttc ttcaatctat      1920
tcattcgttt accaaatatt atttggtaag cactaattat gaatatatat atgttcatgt      1980
tattgatgaa gacaaaattt gatctttgtt tgtttattca ggaactatgc taatgactcc      2040
cgagagaaga agggctatct ggcaatata tggtgaggtt tctagccatt taataacagt       2100
tacgcgcaca aacacatatg attaatcggg gacgagaaaa aagaaatga agtttgagtt       2160 ttgagggtca tatgtaatag gtaaatccga gcttgactag cttgagatgt ttattgtcat      2220
atcatgctca atactaacca aaacactgaa aaagaacttg attatattta catactaata      2280
ttttcatttg cgttgctgtt cacattttta cctatggaac tggttttgt gatttgttat       2340 acttcatatt cgatgttaat aaaatatatc attcctccct ttttctccac ttcaagcttt      2400
actgtagtgt tgaaaggga aactccttt aatgattgca tatataaacg aacttcttga        2460
gttgaatagt ttctcattat gatctgttta acagtatgg tgcagaagaa cagatgaact       2520
tgttgatggc ccaaacgcat catatattac cccggcagcc ttagataggt gggaaaatag      2580
gctagaagat gttttcaatg ggcggccatt tgacatgctc gatggtgctt tgtccgatac      2640
agtttctaac tttccagttg atattcaggt tagtctacca attctatggt ctttatattt      2700
gttcaatttg cgtttgatgt cacttttgct gagggctttt ctaatagctt acttcagcct      2760
agcggaaatg tttgtagttg aatctctagt tctgtctcct atatctgttt ctctcgtcct      2820
agatactaca catacttcat ttctgtttta acatttatt cgtcttttgg tgttgttttg       2880
tatgtgaatc atatatttgg aacagaatca ttattagttc acatgatttc atttgctttc     2940
ttcaatagcg taattgtcta accttccaat atatgttgca gccattcaga gatatgattg      3000
aaggaatgcg tatggacttg agaaaatcga gatacaaaaa cttcgacgaa ctataccttt     3060
attgttatta tgttgctggt acggttgggt tgatgagtgt tccaattatg ggtatcgccc      3120
ctgaatcaaa ggcaacaaca gagagcgtat ataatgctgc tttggctctg gggatcgcaa      3180
atcaattaac taacatactc agagatgttg gagaagagta agtacaaagc tgtgttttac     3240
gcacataatt ttttttgcta atatttacat atcaaaatat aggaaaatga gctcttcggt      3300
tatccggttt atattttttt tatgtcaaca taatagtata agtaattag tatcagtcgt       3360 tctgggaata aaattgcaga actcaattta gccgtgttgt gaaatcctgc ttgttttgag      3420
agcttaaagc tcattagtta gtcgttagag acgaagaaat tcttcgttgt ccatctttat      3480
tccaccttaa agttgtgata ttttcattat tggtacattt ggcaaaaaca cctgaacaaa      3540
tttatgacgg atgcctttg aaagtcacta tacctgtcta gtcggcgttt atcacatttc       3600
tttgacatat tgaactttga aacatgatat cagctctaga cagtgacgag ccatgatcaa      3660
tttctttcct ttattctttc tttggaagtg ccgtatttag gcttccgttg ttcttatata     3720
ttgctttccc tgcagtgcca gaagaggaag agtctacttg cctcaagatg aattagcaca      3780
ggcaggtcta tccgatgaag atatatttgc tggaagggtg accgataaat ggagaatctt      3840
tatgaagaaa caaatacata gggcaagaaa gttctttgat gaggcagaga aaggcgtgac     3900
agaattgagc tcagctagta gattccctgt aagcattcgt aaactcttta gttttatgaa      3960
atgattcttt tttcgcgtta ttagatgaat atggttgctt gtgttgagta tttctaggtc     4020
gatgaagttg agacaagggt ttttaagttt taacgacttt tacggggtgc catgttatct      4080
gctacctaat cttaggtagt tgaccggaag ggctagaatt ttaacctcat gttcaccta      4140
```

```
ccaaccaaga aatgaacctc gcatagagct cgtagttatg aatatttgct ttggcatgac    4200
attgtgcgga tcatgaaatg tcttagatta tatggaaaaa tcattctatt acatcgaata    4260
gatacattag atctaagaag cacgccgtgt tgtaaatgag aaattctata gctcagatct    4320
ttagttttct ctgaacgacc tacaaaccaa cggataacct tgtattgagc ttgtcgttct    4380
cagtatttgc actaacatta cgtcgtgtgg atcctgaaat ggcttggatt gctattattc    4440
tggatatggc aaaaccattt tattagtact agatatcgaa taactacatt tgaccctaca    4500
agtaccctgg gttggagtta caatatccca tacctcgtat ctttagtgtt ctcttattta    4560
tcacctttgt ctactattct ggcaaaataa cctcactcgt tactcggtgt tttccaggta    4620
tgggcatctt tggtcttgta ccgcaaaata ctagatgaga ttgaagccaa tgactacaac    4680
aacttcacaa agagagcata tgtgagcaaa tcaaagaagt tgattgcatt acctattgca    4740
tatgcaaaat ctcttgtgcc tcctacaaaa actgcctctc ttcaaagata aagcatgaaa    4800
tgaagatata tatatatata tatatagcaa tatacattag aagaaaaaaa ggaagaagaa    4860
atgttgttgt attgatataa atgtatatca taaatattag gttgtagtaa cattcaatat    4920
aattatctct tgtagttgtt gtatcttcac tttatctcaa ctcctttgag agaactttcc    4980
gtagttatct gctttgcact tggttactca gaatttcact gtgggcatga taattgatat    5040
accaaattca gttttgattc tatcgaaaaa tttgttatta cattttttg gggggaaagg    5100 aa                                                                   5102

<210> SEQ ID NO 7
<211> LENGTH: 17
<212> TYPE: DNA
<213> ORGANISM: Artificial Sequence
<220> FEATURE:
<223> OTHER INFORMATION: Synthetic polynucleotide

<400> SEQUENCE: 7
tctggataat ctggata                                                     17

<210> SEQ ID NO 8
<211> LENGTH: 3994
<212> TYPE: DNA
<213> ORGANISM: Lycopersicon

<400> SEQUENCE: 8
gatttcacta tattgtaata ttaacttgag gtcactatag gagctcaaaa acttctaatt      60
ttgaatcaat gtctggttat acttttttttg tcataactgt atctcaaatg tggtgtttgg    120
tttatctcat tttgcagaag tcaagaaaca ggttactcct gtttgagtga ggaaaagttg    180
gtttgcctgt ctgtggtctt tttataatct ttttctacag aagagaaagt gggtaatttt    240
gtttgagagt ggaaatattc tctagtggga atctactagg agtaatttat tttctataaa    300
ctaagtaaag tttggaaggt gacaaaaaga aagacaaaaa tcttggaatt gttttagaca    360
accaaggttt tcttgctcag aatgtctgtt gccttgttat gggttgtttc tccttgtgac    420
gtctcaaatg ggacaagttt catggaatca gtccgggagg gaaaccgttt ttttgattca    480
tcgaggcata ggaatttggt gtccaatgag agaatcaata gaggtggtgg aaagcaaact    540
aataatggac ggaaattttc tgtacggtct gctattttgg ctactccatc tggagaacgg    600
acgatgacat cggaacagat ggtctatgat gtggttttga ggcaggcagc cttggtgaag    660
aggcaactga gatctaccaa tgagttagaa gtgaagccgg atatacctat tccggggaat    720
```

-continued

```
ttgggcttgt tgagtgaagc atatgatagg tgtggtgaag tatgtgcaga gtatgcaaag       780
acgtttaact taggttagct tcttcaatct attcattcgt ttaccaaata ttatttggta       840
agcactaatt atgaatatat atatgttcat gttattgatg aagacaaaat ttgatctttg       900
tttgttattt caggaactat gctaatgact cccgagagaa gaagggctat ctaggcaata       960
tatggtgagg tttctagcca tttaataaca gttacgcgca caaacacata tgattaatcg      1020
gggacgagaa aaaagaaat gaagtttgag ttttgagggt catatgtaat aggtaaatcc       1080
gagcttgact agcttgagat gtttattgtc atatcatgct caatactaac caaaacactg      1140
aaaaagaact tgattatatt tacatactaa tattttcatt tgcgttgctg ttcacatttt      1200
tacctatgga actggttttt gtgatttgtt atacttcata ttcgatgtta ataaaatata      1260
tcattcctcc cttttttctcc acttcaagct ttactgtagt gttgaaaggg gaaactcctt     1320
ttaatgattg catatataaa cgaacttctt gagttaata gtttctcatt atgatctgtt       1380
taaacagtat ggtgcagaag aacagatgaa cttgttgatg gcccaaacgc atcatatatt      1440
accccggcag ccttagatag gtgggaaaat aggctagaag atgttttcaa tgggcggcca      1500
tttgacatgc tcgatggtgc tttgtccgat acagtttcta actttccagt tgatattcag      1560
gttagtctac caattctatg gtcttatat ttgttcaatt tgcgtttgat gtcactttg       1620 ctgagggctt ttctaatagc ttacttcagc ctagcggaaa tgtttgtagt gaatctcta      1680 gttctgtctc ctatatctgt ttctctcgtc ctagatacta cacatacttc atttctgttt     1740 taacattta ttcgtctttt ggtgttgttt tgtatgtgaa tcatatatttt ggaacagaat      1800 cattattagt tcacatgatt tcatttgctt tcttcaatag cgtaattgtc taaccttcca     1860
atatatgttg cagccattca gagatatgat tgaaggaatg cgtatggact tgagaaaatc      1920
gagatacaaa aacttcgacg aactatacct ttattgttat tatgttgctg gtacggttgg     1980
gttgatgagt gttccaatta tgggtatcgc ccctgaatca aaggcaacaa cagagagcgt     2040
atataatgct gctttggctc tggggatcgc aaatcaatta actaacatac tcagagatgt     2100
tggagaagag taagtacaaa gctgtgtttt acgcacataa ttttttttgc taatatttac     2160
atatcaaaat ataggaaaat gagctcttcg gttatccggt ttatattttt tttatgtcaa     2220
cataatagta taaagtaatt agtatcagtc gttctgggaa taaaattgca gaactcaatt     2280
tagccgtgtt gtgaaatcct gcttgttttg agagcttaaa gctcattagt tagtcgttag     2340
agacgaagaa attcttcgtt gtccatcttt attccaccttt aaagttgtga tattttcatt    2400
attggtacat ttggcaaaaa cacctgaaca aatttatgac ggatgccttt tgaaagtcac     2460
tatacctgtc tagtcggcgt ttatcacatt tctttgacat attgaacttt gaaacatgat     2520
atcagctcta gacagtgacg agccatgatc aatttctttc ctttattctt tctttggaag    2580
tgccgtattt aggcttccgt tgttcttata tattgctttc cctgcagtgc cagaagagga     2640
agagtctact tgcctcaaga tgaattagca caggcaggtc tatccgatga agatatattt     2700
gctggaaggg tgaccgataa atggagaatc tttatgaaga aacaaataca tagggcaaga    2760
aagttctttg atgaggcaga gaaaggcgtg acagaattga gctcagctag tagattccct     2820
gtaagcattc gtaaactctt tagttttatg aaatgattct ttttcgcgt tattagatga     2880 atatggttgc ttgtgttgag tatttctagg tcgatgaagt tgagacaagg gttttttaagt   2940 tttaacgact tttacgggt gccatgttat ctgctaccta atcttaggta gttgaccgga     3000
agggctagaa ttttaacctc atgttcaccc taccaaccaa gaaatgaacc tcgcatagag     3060
ctcgtagtta tgaatatttg ctttggcatg acattgtgcg gatcatgaaa tgtcttagat    3120
```

-continued

```
tatatggaaa aatcattcta ttacatcgaa tagatacatt agatctaaga agcacgccgt    3180
gttgtaaatg agaaattcta tagctcagat ctttagtttt ctctgaacga cctacaaacc    3240
aacggataac cttgtattga gcttgtcgtt ctcagtattt gcactaacat tacgtcgtgt    3300
ggatcctgaa atggcttgga ttgctattat tctggatatg gcaaaaccat tttattagta    3360
ctagatatcg aataactaca tttgaccccta caagtaccct gggttggagt tacaatatcc    3420
catacctcgt atctttagtg ttctcttatt tatcacctttt gtctactatt ctggcaaaat    3480
aacctcactc gttactcggt gttttccagg tatgggcatc tttggtcttg taccgcaaaa    3540
tactagatga gattgaagcc aatgactaca acaacttcac aaagagagca tatgtgagca    3600
aatcaaagaa gttgattgca ttacctattg catatgcaaa atctcttgtg cctcctacaa    3660
aaactgcctc tcttcaaaga taaagcatga aatgaagata tatatatata tatatatagc    3720
aatatacatt agaagaaaaa aaggaagaag aaatgttgtt gtattgatat aaatgtatat    3780
cataaatatt aggttgtagt aacattcaat ataattatct cttgtagttg ttgtatcttc    3840
actttatctc aactcctttg agagaacttt ccgtagttat ctgcttttgca cttggttact    3900 cagaatttta ctgtgggcat gataattgat ataccaaatt cagttttgat tctatcgaaa    3960
aatttgttat tacattttttt tgggggggaaa ggaa                              3994

<210> SEQ ID NO 9
<211> LENGTH: 3993
<212> TYPE: DNA
<213> ORGANISM: Lycopersicon

<400> SEQUENCE: 9
gatttcacta tattgtaata ttaacttgag gtcactatag gagctcaaaa acttctaatt      60
ttgaatcaat gtctggttat actttttttg tcataactgt atctcaaatg tggtgtttgg     120
tttatctcat tttgcagaag tcaagaaaca ggttactcct gtttgagtga ggaaaagttg     180
gtttgcctgt ctgtggtctt tttataatct ttttctacag aagagaaagt gggtaatttt     240
gtttgagagt ggaaatattc tctagtggga atctactagg agtaatttat tttctataaa     300
ctaagtaaag tttggaaggt gacaaaaaga aagacaaaaa tcttggaatt gttttagaca     360
accaaggttt tcttgctcag aatgtctgtt gccttgttat gggttgtttc tccttgtgac     420
gtctcaaatg ggacaagttt catggaatca gtccgggagg gaaaccgttt ttttgattca     480
tcgaggcata ggaatttggt gtccaatgag agaatcaata gaggtggtgg aaagcaaact     540
aataatggac ggaaatttttc tgtacggtct gctattttgg ctactccatc tggagaacgg     600
acgatgacat cggaacagat ggtctatgat gtggttttga ggcaggcagc cttggtgaag     660
aggcaactga gatctaccaa tgagttagaa gtgaagccgg atatacctat tccgggggaat    720 ttgggcttgt tgagtgaagc atatgatagg tgtggtgaag tatgtgcaga gtatgcaaag    780
acgtttaact taggttagct tcttcaatct attcattcgt ttaccaaata ttatttggta    840
agcactaatt atgaatatat atatgttcat gttattgatg aagacaaaat ttgatctttg    900
tttgtttatt caggaactat gctaatgact cccgagagaa gaagggctat ctgggcaata    960
tatggtgagg tttctagcca tttaataaca gttacgcgca caaacacata tgattaatcg   1020
gggacgagaa aaaagaaat gaagtttgag ttttgagggt catatgtaat aggtaaatcc   1080
gagcttgact agcttgagat gtttattgtc atatcatgct caatactaac caaaacactg   1140
aaaaagaact tgattatatt tacatactaa tattttcatt tgcgttgctg ttcacatttt   1200
```

```
tacctatgga actggttttt gtgatttgtt atacttcata ttcgatgtta ataaaatata   1260
tcattcctcc ctttttctcc acttcaagct ttactgtagt gttgaaaggg gaaactcctt   1320
ttaatgattg catatataaa cgaacttctt gagttgaata gtttctcatt atgatctgtt   1380
taaacagtat ggtgcagaag aacagatgaa cttgttgatg gcccaaacgc atcatatatt   1440
accccggcag ccttagatag gtgggaaaat aggctagaag atgttttcaa tgggcggcca   1500
tttgacatgc tcgatggtgc tttgtccgat acagtttcta actttccagt tgatattcag   1560
gttagtctac caattctatg gtctttatat ttgttcaatt tgcgtttgat gtcacttttg   1620
ctgagggctt ttctaatagc ttacttcagc ctagcgaaaa tgtttgtagt tgaatctcta   1680
gttctgtctc ctatatctgt ttctctcgtc ctagatacta cacatacttc atttctgttt   1740
taacattta ttcgtctttt ggtgttgttt tgtatgtgaa tcatatattt ggaacagaat   1800
cattattagt tcacatgatt tcatttgctt tcttcaatag cgtaattgtc taaccttcca   1860
atatatgttg cagccattca gagatatgat tgaaggaatg cgtatggact tgagaaaatc   1920
gagatacaaa aacttcgacg aactataccT ttattgttat tatgttgctg gtacggttgg   1980
gttgatgagt gttccaatta tgggtatcgc ccctgaatca aaggcaacaa cagagagcgt   2040
atataatgct gctttggctc tggggatcgc aaatcaatta actaacatac tcagagatgt   2100
tggagaagag taagtacaaa gctgtgtttt acgcacataa tttttttgc taatatttac   2160
atatcaaaat ataggaaaat gagctcttcg gttatccggt ttatatttt tttatgtcaa   2220
cataatagta taaagtaatt agtatcagtc gttctgggaa taaaattgca gaactcaatt   2280
tagccgtgtt gtgaaatcct gcttgttttg agagcttaaa gctcattagt tagtcgttag   2340
agacgaagaa attcttcgtt gtccatcttt attccacctt aaagttgtga tattttcatt   2400
attggtacat ttggcaaaaa cacctgaaca aatttatgac ggatgccttt tgaaagtcac   2460
tatacctgtc tagtcggcgt ttatcacatt tctttgacat attgaacttt gaaacatgat   2520
atcagctcta gacagtgacg agccatgatc aatttctttc ctttattctt tctttggaag   2580
tgccgtattt aggcttccgt tgttcttata tattgctttc cctgcagtgc cagaagagga   2640
agagtctact tgcctcaaga tgaattagca caggcaggtc tatccgatga agatatattt   2700
gctggaaggg tgaccgataa atggagaatc tttatgaaga aacaaataca tagggcaaga   2760
aagttctttg atgaggcaga gaaaggcgtg acagaattga gctcagctag tagattccct   2820
gtaagcattc gtaaactctt tagttttatg aaatgattct ttttcgcgt tattagatga   2880
atatggttgc ttgtgttgag tatttctagg tcgatgaagt tgagacaagg gttttaagt   2940
tttaacgact tttacggggt gccatgttat ctgctaccta atcttaggta gttgaccgga   3000
agggctagaa ttttaacctc atgttcaccc taccaaccaa gaaatgaacc tcgcatagag   3060
ctcgtagtta tgaatatttg ctttggcatg acattgtgcg gatcatgaaa tgtcttagat   3120
tatatggaaa aatcattcta ttacatcgaa tagatacatt agatctaaga agcacgccgt   3180
gttgtaaatg agaaattcta tagctcagat ctttagtttt ctctgaacga cctacaaacc   3240
aacggataac cttgtattga gcttgtcgtt ctcagtattt gcactaacat tacgtcgtgt   3300
ggatcctgaa atggcttgga ttgctattat tctggatatg gcaaaaccat tttattagta   3360
ctagatatcg aataactaca tttgacccta caagtaccct gggttggagt tacaatatcc   3420
catacctcgt atctttagtg ttctcttatt tatcaccttt gtctactatt ctggcaaaat   3480
aacctcactc gttactcggt gttttccagg tatgggcatc tttggtcttg taccgcaaaa   3540
tactagatga gattgaagcc aatgactaca acaacttcac aaagagagca tatgtgagca   3600
```

```
aatcaaagaa ttgattgcat tacctattgc atatgcaaaa tctcttgtgc ctcctacaaa    3660
aactgcctct cttcaaagat aaagcatgaa atgaagatat atatatatat atatatagca    3720
atatacatta gaagaaaaaa aggaagaaga aatgttgttg tattgatata aatgtatatc    3780
ataaatatta ggttgtagta acattccaata taattatctc ttgtagttgt tgtatcttca    3840
ctttatctca actcctttga gagaacttte cgtagttatc tgctttgcac ttggttactc    3900
agaattttac tgtgggcatg ataattgata taccaaattc agttttgatt ctatcgaaaa    3960
atttgttatt acattttttt gggggaaag gaa                                  3993

<210> SEQ ID NO 10
<211> LENGTH: 19
<212> TYPE: DNA
<213> ORGANISM: Artificial Sequence
<220> FEATURE:
<223> OTHER INFORMATION: Synthetic polynucleotide (primer)

<400> SEQUENCE: 10
cagtgccaga agaggaaga                                                 19

<210> SEQ ID NO 11
<211> LENGTH: 20
<212> TYPE: DNA
<213> ORGANISM: Artificial Sequence
<220> FEATURE:
<223> OTHER INFORMATION: Synthetic polynucleotide (primer)

<400> SEQUENCE: 11
ttgcggtaca agaccaaaga                                                20

<210> SEQ ID NO 12
<211> LENGTH: 20
<212> TYPE: DNA
<213> ORGANISM: Artificial Sequence
<220> FEATURE:
<223> OTHER INFORMATION: Synthetic polynucleotide (primer)

<400> SEQUENCE: 12
gtggatcctg aaatggcttg                                                20

<210> SEQ ID NO 13
<211> LENGTH: 23
<212> TYPE: DNA
<213> ORGANISM: Artificial Sequence
<220> FEATURE:
<223> OTHER INFORMATION: Synthetic polynucleotide (primer)

<400> SEQUENCE: 13
agtactaata aatggtttt gcc                                             23

<210> SEQ ID NO 14
<211> LENGTH: 19
<212> TYPE: DNA
<213> ORGANISM: Artificial Sequence
<220> FEATURE:
<223> OTHER INFORMATION: Synthetic polynucleotide (primer)

<400> SEQUENCE: 14
gggctagtcg gtgtatcat                                                 19

<210> SEQ ID NO 15
<211> LENGTH: 20
<212> TYPE: DNA
```

<213> ORGANISM: Artificial Sequence
<220> FEATURE:
<223> OTHER INFORMATION: Synthetic polynucleotide (primer)

<400> SEQUENCE: 15
ctggaagggt gaccgataaa                                              20

<210> SEQ ID NO 16
<211> LENGTH: 19
<212> TYPE: DNA
<213> ORGANISM: Artificial Sequence
<220> FEATURE:
<223> OTHER INFORMATION: Synthetic polynucleotide (primer)

<400> SEQUENCE: 16
atgatacacc gactagccc                                               19

<210> SEQ ID NO 17
<211> LENGTH: 23
<212> TYPE: DNA
<213> ORGANISM: Artificial Sequence
<220> FEATURE:
<223> OTHER INFORMATION: Synthetic polynucleotide (primer)

<400> SEQUENCE: 17
ctgtgaatgc tgcgactacg att                                          23

<210> SEQ ID NO 18
<211> LENGTH: 22
<212> TYPE: DNA
<213> ORGANISM: Artificial Sequence
<220> FEATURE:
<223> OTHER INFORMATION: Synthetic polynucleotide (primer)

<400> SEQUENCE: 18
ctgtgaatgc tgcgactacg at                                           22

<210> SEQ ID NO 19
<211> LENGTH: 20
<212> TYPE: DNA
<213> ORGANISM: Artificial Sequence
<220> FEATURE:
<223> OTHER INFORMATION: Synthetic polynucleotide (primer)

<400> SEQUENCE: 19
aacttgttga tggcccaaac                                              20

<210> SEQ ID NO 20
<211> LENGTH: 22
<212> TYPE: DNA
<213> ORGANISM: Artificial Sequence
<220> FEATURE:
<223> OTHER INFORMATION: Synthetic polynucleotide (primer)

<400> SEQUENCE: 20
agccattcag agatatgatt ga                                           22

<210> SEQ ID NO 21
<211> LENGTH: 20
<212> TYPE: DNA
<213> ORGANISM: Artificial Sequence
<220> FEATURE:
<223> OTHER INFORMATION: Synthetic polynucleotide (primer)

<400> SEQUENCE: 21
atcggataga cctgcctgtg                                              20

-continued

<210> SEQ ID NO 22
<211> LENGTH: 21
<212> TYPE: DNA
<213> ORGANISM: Artificial Sequence
<220> FEATURE:
<223> OTHER INFORMATION: Synthetic polynucleotide (primer)

<400> SEQUENCE: 22
ttatctttga agagaggcag t                                        21

<210> SEQ ID NO 23
<211> LENGTH: 22
<212> TYPE: DNA
<213> ORGANISM: Artificial Sequence
<220> FEATURE:
<223> OTHER INFORMATION: Synthetic polynucleotide (primer)

<400> SEQUENCE: 23
gataaagtga agatacaaca ac                                       22

<210> SEQ ID NO 24
<211> LENGTH: 744
<212> TYPE: PRT
<213> ORGANISM: Lycopersicon

<400> SEQUENCE: 24

Met Glu Ser Ser Lys Lys Ser Gly Ser Lys Lys Gly Leu Val Glu Ser
1               5                   10                  15

Val Lys Lys Leu Val Lys Thr Asn Lys Gly Ala Ser Ser Ser Lys
            20                  25                  30

Ser Lys Ile Pro Leu Val Arg Ile Asn Thr Asp Glu Phe Thr His Val
        35                  40                  45

Asn Glu Thr Ser Phe Ser Arg Pro Gly Pro Ile Asn Ile Asn Ser Asp
    50                  55                  60

Ser Pro Thr Pro His Glu Leu Tyr Glu Arg Tyr Tyr Gly Ile Asn Gln
65                  70                  75                  80

Glu Asn Glu Glu Val Glu Thr Asp Glu Gln Leu Asn Leu Asp Glu Glu
                85                  90                  95

Val Asp Leu Asp Asp Thr Pro Thr Ser Pro Ala Ala Asp Leu Asn Thr
            100                 105                 110

Val Asn Ser Ile Gly Ile Glu Ala Pro Pro Val Gly Thr Thr Arg
        115                 120                 125

Pro Leu Ile Ile Pro Thr Arg Gly Lys Thr Lys Val Gln Arg Ser Leu
    130                 135                 140

Lys Ser His Val Trp Lys Phe Cys Tyr Leu Asn Glu Glu Lys Thr Phe
145                 150                 155                 160

Ser Ile Cys Asn Leu Cys Lys Gln His Phe Lys Tyr Thr Ser Gly Gly
                165                 170                 175

Thr Gly Gly Ser Thr Gly Gly Leu Lys Lys His Leu Ile Asn Lys His
            180                 185                 190

Ser Lys Glu Trp Phe Ala Tyr Met Ser Ser Leu Glu Val Gly Gly Asn
        195                 200                 205

Cys Asn Val Glu Glu Ser Val Arg Gly Ser Asn Met Val Gln Ser Glu
    210                 215                 220

Leu Asn Thr Ser Asn Pro Ser Gly Pro Leu Thr His Arg Thr Tyr Asn
225                 230                 235                 240

Lys Asp Arg Asp Arg Glu Asn Phe Ala Lys Met Val Val Val Cys Gly

```
            245                 250                 255
Leu Pro Phe Ser Phe Gly Glu His Pro Gly Phe Ile Ala Tyr Ile Arg
            260                 265                 270

Glu Thr Tyr Asn Pro Ser Phe Gln Gly Leu Ser Arg Ser Met Val Lys
            275                 280                 285

Arg Asp Ile Phe Glu Phe Gln Glu Lys His Cys Gln Tyr Leu Arg Ala
            290                 295                 300

Tyr Phe Glu Leu Met Asp Cys Arg Val Ala Ile Thr Thr Asp Met Gly
305                 310                 315                 320

Arg Ser Pro Asn Gly Phe Asp Tyr Leu Thr Val Thr Ala His Trp Ile
            325                 330                 335

Asp Tyr Asn Trp Asn Leu Gln Lys Arg Ile Ile Gly Tyr Lys Ile Cys
            340                 345                 350

Gln Lys Lys Lys Thr Gly Ile Tyr Ile Ala Thr Thr Val Leu Glu Ile
            355                 360                 365

Leu Asp Phe Phe Gly Leu Cys Asp Lys Val Val Ser Ile Thr Leu Asp
            370                 375                 380

Asn Ala Ser Ala Asn Leu Asn Ala Ile Asn Leu Leu Glu Pro Arg Leu
385                 390                 395                 400

Cys Pro Ile Ser Lys Tyr Ala Phe His Val Arg Cys Ala Ala His Ile
                    405                 410                 415

Leu Asn Leu Val Val Ser Asp Gly Val Lys Leu Phe Glu Asn Ser Cys
                    420                 425                 430

Asp Lys Ile Asp Asn Ala Cys Phe Tyr Ile Phe His Met Asn Ser Ser
            435                 440                 445

Ser Arg Ile Asn Gln Phe Lys Glu Leu Cys Asn Ala Phe Lys Leu Pro
            450                 455                 460

Phe Arg Lys Val Pro Lys His Val Lys Thr Arg Trp Asn Ser Phe Tyr
465                 470                 475                 480

Asp Met Leu Glu Val Ala Tyr Ala Tyr Arg Gln Pro Ile Thr Thr Leu
                    485                 490                 495

Phe Asn Asn His Asn Ala Tyr Pro Glu Phe Lys Ile Asn Asp Ser Asp
            500                 505                 510

Trp Asp Glu Val Asn Glu Leu Arg Ile Phe Leu Lys Ser Phe Tyr Asp
            515                 520                 525

Ala Thr Lys Ile Phe Ser Gly Ile Tyr Tyr Pro Thr Ile Ser Glu Ile
            530                 535                 540

Leu Ile His Ile Cys Glu Ile Ser Ser Ile Phe Ser Glu Tyr Lys Thr
545                 550                 555                 560

Asn Thr Leu Phe Thr Ser Ala Ile Glu Val Met Ile Thr Lys Phe Lys
                    565                 570                 575

Lys Tyr Phe Phe Pro Ile Pro Gln Ile Tyr Leu Thr Ala Leu Leu Phe
            580                 585                 590

Asn Pro Glu Tyr Lys Glu Tyr Gly Thr Lys Ala Leu Val Glu Cys Ile
            595                 600                 605

Tyr Gln Asn Leu Asp Ile Gln Pro Glu Glu Pro Asp Leu Val Thr
            610                 615                 620

Cys Gln Asn Ser Ile Lys Tyr Phe Ala Lys Glu Met Tyr Asp Lys Tyr
625                 630                 635                 640

Ser Phe Leu Asp Asn Val Glu Asn Pro Gln Thr Ser Thr Asn Gln Val
                    645                 650                 655

Gly Ala His Gly Arg Val Lys His Lys Leu Gly Leu Asp Ser Ser Asn
            660                 665                 670
```

```
Lys Cys Glu Phe Val Lys Tyr Leu Glu Gln Gly Thr Asp Asp Ile Thr
            675                 680                 685

Asn Asp Asn Gly Ile Pro Glu Leu Leu Asn Trp Trp Arg Asn Arg Gly
        690                 695                 700

Ala Gln Tyr Pro Lys Leu Ser Arg Met Val Lys Asp Val Leu Ala Ile
705                 710                 715                 720

Gln Gly Ser Ser Val Val Arg Arg Gln Leu Ser Ala Arg Gln Asp Phe
                725                 730                 735

Lys Leu Glu Thr Thr Asp Ile Arg
            740

<210> SEQ ID NO 25
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 25
gtggatcctg aaatggcttg gattgctatt attctggata tggcaaaac                49

<210> SEQ ID NO 26
<211> LENGTH: 58
<212> TYPE: DNA
<213> ORGANISM: Artificial Sequence
<220> FEATURE:
<223> OTHER INFORMATION: Synthetic Polynucleotide

<400> SEQUENCE: 26
gtggatcctg aaatggcttg gattgctatt attctggata atctggatat ggcaaaac     58

<210> SEQ ID NO 27
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 27
gtggatcctg aaatggcttg gattgctatt attctggatc tggatatggc aaaac        55

<210> SEQ ID NO 28
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 28
gtggatcctg aaatggcttg gattgctatt attccggata atatggcaaa ac           52

<210> SEQ ID NO 29
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 29
gtggatcctg aaatggcttg gattgctatt attctggatt ctggatatgg caaaac       56
```

TOMATO PLANTS HAVING FRUIT WITH YELLOW AND RED SEGMENTS

SEQUENCE LISTING

The Sequence Listing submitted in text format (.txt) filed on Aug. 10, 2018, named "SequenceListing.txt", created on Aug. 10, 2018, 49.7 KB), is incorporated herein by reference.

FIELD OF THE INVENTION

The present invention relates to tomato plants having fruit with bicolor red-yellow flesh and epidermis, comprising within their genome an insertion mutation within the Phytoene synthase 1 (Psy1) gene.

BACKGROUND OF THE INVENTION

Tomato is a basic nutritional component in many cultures worldwide. It is known for its vitamin, mineral and antioxidant content that provide the consumers with these health beneficial components. A large number of tomato varieties is available in the market, and it is recognized that in addition to the nutritional and taste parameters, color and general appearance influence the purchase of tomato fruit by private as well as cuisine professional customers.

Tomato fruit color is furnished by lycopene, a linear carotene molecule with 11 conjugated double bonds, which accumulates to high concentration within chromoplasts during fruit ripening. Biosynthesis of lycopene is mainly controlled at the gene expression level of carotenoid-biosynthesis enzymes. During fruit ripening, genes for enzymes upstream to lycopene are upregulated whereas genes for lycopene cyclases, which metabolize lycopene to alpha- and beta-carotene, are silenced.

The improvement of crop species has been a fundamental human pursuit since the beginning of agriculture. One can imagine that unique plant phenotypes, sometimes represented even by a single plant, caught the eyes of the first ancient breeders. The manner in which the improvement process was done constituted a founder effect which is often manifested in severe genetic bottlenecks. As a result of these genetic bottlenecks imposed during early domestication and modern breeding activities, cultivated varieties of most crop species carry only a small fraction of the variation presented in their wild ancestors and land races (Tanksley S D and McCouch S R. 1997. Science 277:1063-1066). The narrowed genetic variation in modern crops is one of the causes for genetic vulnerability to various plant diseases and pests. Moreover, it presents a breeding obstacle by lowering the chance of obtaining better gene and allelic combinations to improve traits with agricultural importance.

One of the most powerful and efficient method in the area of genetics, molecular biology and plant breeding is based on mutant variation. Mutation is the major evolutionary force that creates variation to improve survivability of existing diversity and for the evolution of novel ecotypes, races and species. However, since the frequency of spontaneous mutants is very low, they supply information on a relatively small number of genes and biological phenomena. Therefore, artificial mutagenesis methods have been developed and are being applied to induce variation. Induced variation is in turn used as a tool for the discovery of gene function and for understanding developmental processes.

An available source of tomato mutations is an isogenic tomato "mutation library" generated in the genetic background of the processing tomato inbred variety M82, by one of the inventors of the present invention and co-workers (Menda N et al., 2004. Plant J. 38:861-872). For generating the library, a total of 13,000 M2 families, derived from ethyl methanesulfonate (EMS) chemical treatment and from fast-neutron mutagenesis of seeds, were phenotyped when grown under field conditions. Based on the phenotypes, the families were categorized into a morphological catalog that included 15 primary and 48 secondary categories. More than 3000 mutations have been identified in this library. Some of the mutations represent new alleles of previously described phenotypes from the monogenic mutant collection of The Tomato Genetics Resource Center (TGRC), most of which in the M82 isogenic population. In addition, over 1,000 novel phenotypes with multiple alleles per locus were identified.

Results of allelism tests between mutants sharing similar phenotypes verified the hypothesis that the population is reaching saturation, with hits in the majority of the genes (for example, from the dominant LANCEOLATE mutation 8 independent alleles where identified; from the yellow fruited Yellow flesh mutation 5 alleles were obtained). In addition, screening of 1,000 EMS families subjected to two treatments of EMS did not result in novel phenotypes.

The potential of wild species as a source of genetic variation to bring about crop improvement was recognized early in the twenty first century (Zamir D. 2001. Nat Rev Genet. 2:983-989). Initial interspecific breeding attempts met with severe problems, including incompatibility in crosses between the wild species and the cultivated crops; F1-hybrid sterility; infertility of the segregating generations; reduced recombination between the chromosomes of the wild species and the cultivated crop; and tight linkage between genes that have negative effects and the traits of interest (McCouch S. 2004. PLoS Biol. 2). Despite these obstacles, there are many examples in which wild introgression breeding has made a considerable contribution to the development of modern-day varieties, predominantly as a source for monogenic or sometimes called single gene traits and to a smaller extent for complex traits such as yield, compositional quality and resistance to various stresses that are influenced by quantitative trait loci (QTL; Fernie A R et al., 2006. Curr. Opin. Plant Biol. 9:196-202).

Notwithstanding the above-described tools for generating new tomato phenotypes, there is a constant market demand for stable cultivars having fruit with new, attractive color.

SUMMARY OF THE INVENTION

The present invention relates to tomato cultivars producing fruit with yellow-red segments across the entire fruit, from the internal placenta and/or locules and to the external epidermis layer of the pericarp. This yellow-red stripe phenotype, designated herein Arlecchino, can include from one stripe or segment of each color in a single fruit to multiple number of stripes of each color in the fruit. In contrast to hitherto known fruit with alternate yellow-red skin phenotype, the Arlecchino phenotype shows the color section across the entire fruit.

The present invention further relates to seeds of the plants of the present invention, to plants grown from the seeds, to their progeny, to fruit produced by the plants, to plant parts derived therefrom and to methods of producing same.

The present invention is based in part on the unexpected discovery of a mutation in a population of tomato backcross inbred lines originated from a man-made cross of wild species tomato with a commercial cultivar. The mutation, an insertion mutation within the Phytoene synthase 1 (Psy1) gene is linked to the Arlecchino phenotype described above. The yellow sections of the Arlecchino phenotypes result from an insertion within the Psy1 gene, in intron 8 present between exon 8 and exon 9 of the gene (according to the gene structure as depicted in FIG. 8, an update of the structure published by Giorio G et al., 2008. FEBS J. 275:527-535).

The initial insertion observed in yellow sections of the Arlecchino fruit was of nine (9) nucleotide, comprising the nucleic acids sequence ATCTGGATA (SEQ ID NO:1). The position of this insertion within the Psy1 gene indicated a direct repeat of eight (8) nucleotides comprising the nucleic acids sequence TCTGGATA (SEQ ID NO:2) separated by one Adenine (A) nucleotide. Further analysis of the insertion using high-fidelity DNA Polymerase (PrimeSTAR GXL DNA Polymerase (Takara Bio)), cloning and sequencing the amplified polynucleotides revealed an insertion of a transposon flanked by the nucleic acids sequence set forth in SEQ ID NO:2 associated with the Arlecchino phenotype. Nevertheless, a PCR product comprising the nucleic acid sequence TCTGGATAATCTGGATA (SEQ ID NO:7), comprising the direct repeat separate by the Adenine (A) nucleotide is amplified from genetic material obtained from yellow sections of Arlecchino fruit using standard DNA Polymerase (READY-MIX kit (Syntezza).

In cells of the yellow sections the insertion is found in homozygous form. The red sections of the Arlecchino phenotype comprise either wild type Psy1 alleles or Psy1 alleles comprising transposon excision footprint comprising variable sequences of the direct repeat area within the intron.

Without wishing to be bound by any specific theory or mechanism of action, this hitherto unknown mutation may be the result of merging divergent genomes achieved through man-made genetic crossings.

According to one aspect, the present invention provides a tomato cultivar which produces fruit having an Arlecchino phenotype of yellow-red segments spanning from the placenta and/or locules across the fruit pericarp to the epidermis, wherein the phenotype is linked to at least one allele of $r^{arl}$, the $r^{arl}$ allele is Phytoene synthase 1 (Psy1) allele comprising an insertion within an intron of the allele, wherein the insertion results in a non-functional splice variant of Psy1.

According to certain embodiments, cells of the yellow segments of the Arlecchino fruit are homozygous for the $r^{arl}$ allele.

According to certain embodiments, the insertion comprises a transposon flanked by the nucleic acid sequence TCTGGATA (SEQ ID NO:2) at the transposon 3' end. According to additional embodiments, the insertion comprises a transposon flanked by the nucleic acid sequence ATCTGGATA (SEQ ID NO:1) at the transposon 3' end.

According to certain embodiments, the transposon belongs to the hAT family. According to some embodiments, the transposon comprises a nucleic acid sequence at least 90% or at least 95% or more homologous to the nucleic acid sequence set forth in SEQ ID NO:3. Each possibility represents a separate embodiment of the present invention. According to certain exemplary embodiments, the transposon comprises the nucleic acid sequence set forth in SEQ ID NO:3. According to additional exemplary embodiments, the transposon consists of the nucleic acid sequence set forth in SEQ ID NO:3.

According to certain embodiments, the insertion within the Psy1 gene comprises a nucleic acid sequence at least 90%, at least 95% or more homologous to the nucleic acid sequence set forth in SEQ ID NO:4. According to certain exemplary embodiments, the insertion within the Psy1 gene comprises the nucleic acid sequence set forth in SEQ ID NO:4. According to additional exemplary embodiments, the insertion within the Psy1 gene consists of the nucleic acid sequence set forth in SEQ ID NO:4.

According to certain exemplary embodiments, the $r^{arl}$ allele of Psy1 comprises the nucleic acid sequence set forth in SEQ ID NO:5.

According to certain embodiments, the wild type (wt) Psy1 allele comprises the nucleic acid sequence set forth in SEQ ID NO:6.

According to some embodiments, the tomato cultivar comprises at least one pericarp cell homozygous for the $r^{arl}$ allele and at least one pericarp cell comprising at least one wild type Psy1 allele or at least one Psy1 allele comprising transposon excision footprint.

According to certain embodiments, the transposon excision footprint comprises at least one nucleotide deletion within the nucleic acid sequence TCTGGATAATCTGGATA (SEQ ID NO:7). According to some embodiments, the transposon excision footprint comprises at least two, at least three, at least four, at least 5, at least 6, at least 7 or at least 8 nucleotides deletion. Each possibility represents a separate embodiment of the present invention According to some embodiments, the fruit is ripening fruit at the breaker stage and onward. According to some exemplary embodiments, the fruit is a fully ripe fruit.

It is to be explicitly understood that the entire tomato fruit can show the yellow-red stripe or segment phenotype or the stripes/segments can appear only on parts of the fruit. The width of the stripes can also be variable such that a single fruit may comprise from one red segment and one yellow segment covering the entire fruit to a multiple number of narrow red and yellow stripes covering all or part of the fruit. All appearances are encompassed by the present invention.

According to some embodiment, the tomato cultivar produces small fruit (cherry-like fruit). According to certain exemplary embodiments, the tomato cultivar is *Solanum lycopersicum*.

According to additional embodiments, the tomato cultivar further comprises within its genome an additional Psy1 mutant allele encoding for a yellow flesh phenotype. According to some embodiments, the Psy1 gene encoding for the yellow flesh phenotype comprises the nucleic acid sequence set forth in any one of SEQ ID NO:8 and SEQ ID NO:9. According to these embodiments, the Arlecchino tomato cultivar comprises at least one $r^{arl}$ allele, at least one Psy1 mutant allele encoding for a yellow flesh phenotype and at least one wild type Psy1 allele or Psy1 allele comprising transposon excision footprint. According to certain exemplary embodiments, the yellow segments of the Arlecchino fruit comprise one $r^{arl}$ allele and one Psy1 mutant allele encoding for the yellow flesh phenotype and the red segments comprise wild type Psy1 allele and/or Psy1 allele comprising transposon excision footprint.

According to yet additional embodiments, the tomato cultivar is suitable for commercial growth. The tomato cultivars advantageously can further comprise beneficial agronomical traits as are well known in the art including, but not limited to, high germination rate, herbicide resistance, insect resistance, resistance to bacterial, fungal or viral diseases, resistance to various types of non-biotic stress, male sterility, vigorous growth and any combination thereof. These traits may form part of the genetic background of the tomato cultivars or may be introduced by any method as is known to a person skilled in the art, including, but not limited to, breeding, single trait conversion and transformation.

According to another aspect, the present invention provides a tomato cultivar homozygous to the $r^{arl}$ allele, the $r^{arl}$ allele is Phytoene synthase 1 (Psy1) allele comprising an insertion of a transposon flanked by the nucleic acid sequence TCTGGATA (SEQ ID NO:2) at the transposon 3' end, wherein the tomato cultivar produces entirely yellow fruit. According to certain exemplary embodiments, the tomato cultivar producing the entirely yellow fruit is homozygous to the $r^{arl}$ allele comprising the nucleic acid sequence set forth in SEQ ID NO:5.

The present invention also provides seeds of the tomato cultivar of the invention wherein plants grown from the seed produce fruit having an Arlecchino phenotype of yellow-red segments spanning from placenta and/or locules across the fruit pericarp to the epidermis, wherein the phenotype is linked to $r^{arl}$ allele, the $r^{arl}$ allele is Phytoene synthase 1 (Psy1) allele comprising an insertion within an intron of the allele, wherein the insertion results in a non-functional splice variant of Psy1.

Pollen and ovules from the tomato cultivars of the present invention; the seeds produced from same and the plants grown from the seeds and fruit produced by these plants and having the Arlecchino phenotype are also encompassed within the scope of the present invention.

A tissue culture of regenerable cells or parts thereof of the tomato cultivar of the invention, the regenerable cells obtained from a plant part selected from the group consisting of leaves, pollen, embryos, roots, root tips, anthers, flowers, fruit and seeds, is also encompassed within the scope of the present invention, as well as plant regenerated from the tissue culture producing fruit having an Arlecchino phenotype of yellow-red segments spanning from the placenta and/or locules across the fruit pericarp to the epidermis, wherein the phenotype is linked to $r^{arl}$ allele, the $r^{arl}$ allele is Phytoene synthase 1 (Psy1) allele comprising an insertion within an intron of the allele, wherein the insertion results in a non-functional splice variant of Psy1.

The tomato cultivar plants of the present invention can be in the form of stable true-breeding lines or as a more diverse material, all of which comprise within their genome the $r^{arl}$ allele.

According to additional aspect, the present invention provides a tomato fruit having an Arlecchino phenotype of yellow-red segments spanning from the placenta and/or locules across the fruit pericarp to the epidermis, wherein the phenotype is linked to $r^{arl}$ allele in a cultivated tomato plant producing the fruit, the $r^{arl}$ allele is Phytoene synthase 1 (Psy1) allele comprising an insertion within an intron of the allele, wherein the insertion results in a non-functional splice variant of Psy1.

According to certain exemplary embodiments, the fruit having the Arlecchino phenotype comprises at least one cell homozygous for the $r^{arl}$ allele. According to additional exemplary embodiments, the $r^{arl}$ allele comprises the nucleic acid sequence set forth in SEQ ID NO:5.

According to another aspect, the present invention provides a method for producing a tomato cultivar producing fruit having an Arlecchino phenotype of yellow-red segments spanning from the placenta and/or locules across the fruit pericarp to the epidermis, the method comprising introducing into a tomato cultivar producing red fruit or a part thereof a genetic element comprising $r^{arl}$ allele of Phytoene synthase 1, the $r^{arl}$ allele comprises an insertion within an intron of the allele, wherein the insertion results in a non-functional splice variant of Psy1.

According to certain embodiments, the insertion comprises a transposon flanked by the nucleic acid sequence TCTGGATA (SEQ ID NO:2) at the transposon 3' end. According to additional embodiments, the insertion comprises a transposon flanked by the nucleic acid sequence ATCTGGATA (SEQ ID NO:1) at the transposon 3' end.

According to these embodiments, the transposon comprises a nucleic acids sequence at least 95%, 96%, 97%, 98%, 99% or 100% homologous to SEQ ID NO:3. Each possibility represents a separate embodiment of the present invention.

According to certain exemplary embodiments, the Psy1 $r^{arl}$ allele comprises the nucleic acid sequence set forth in SEQ ID NO:5.

Any method as is known in the art can be used to introduce the genetic element comprising the $r^{arl}$ allele into the tomato cultivar producing red fruit or to a part thereof. When the genetic element is introduced to a plant part, including, but not limited to, a seed, a cell or a tissue, the method further comprises regenerating a cultivar tomato plant from the seed, cell or tissue. Any method as is known in the art for regenerating a plant from seeds, cells or tissues can be used.

According to certain embodiments, the genetic element is introduced by crossing the tomato cultivar producing red fruit with a donor tomato plant comprising the genetic element to provide offspring cultivated tomato plants. According to these embodiments, the method further comprises the steps of:
  a. examining a nucleic acid sample obtained from each offspring cultivated tomato plant or par thereof for the presence of $r^{arl}$ allele;
  b. selecting offspring cultivated tomato plants comprising the $r^{arl}$ allele; and
  c. examining the fruit produced by the plants selected in step (b) and electing cultivated tomato plants producing fruit with Arlecchino phenotype.

According to other embodiments, the genetic element is introduced by transforming a plurality of cells of the tomato cultivar producing red fruit with said genetic element. According to these embodiments, the method further comprises:
  a. examining a nucleic acid sample obtained from each transformed cell for the presence of $r^{arl}$ allele;
  b. selecting a plurality of cells comprising the $r^{arl}$ allele;
  c. regenerating the plurality of transformed cells to obtain a plurality of transgenic plants comprising the $r^{arl}$ allele; and
  d. examining the fruit produced by the transgenic plant and selecting plant producing fruit having the Arlecchino phenotype.

According to certain embodiments, the method further comprises selfing, at least once, the selected cultivated tomato plant to produce a progeny and further identifying and selecting cultivated tomato plants comprising the $r^{arl}$ allele and having the Arlecchino phenotype.

Any method as is known in the art for examining the nucleic acid sample for the presence of the $r^{arl}$ allele can be used according to the teachings of the present invention.

According to some embodiments, the present invention provides at least one probe or pair of primers specifically detecting the presence of the $r^{arl}$ allele of Phytoene synthase 1.

According to certain embodiments, the pair of primers is designed to amplify an $r^{arl}$ allele marker comprising the nucleic acid sequence set forth in SEQ ID NO:7 (TCTG-GATAATCTGGATA). According to certain exemplary embodiments, the r$^{ar1}$ allele marker is amplified by a pair of primer comprising the nucleic acid sequence set forth in SEQ ID NO:10 (CAGTGCCAGAAGAGGAAGA) and SEQ ID NO:11 (TTGCGGTACAAGACCAAAGA).

According to additional embodiments, the pair of primers is designed to amplify the full length transposon insertion. According to certain exemplary embodiments, the transposon is amplified by a pair of primer comprising the nucleic acid sequence set forth in SEQ ID NO:12 (GTGGATCCT-GAAATGGCTTG) and SEQ ID NO:13 (AG-TACTAATAAAATGGTTTTGCC).

According to yet additional embodiments, the pair of primers is designed to amplify the 3' genomic junction of the transposon insertion within the Psy1 allele. According to certain exemplary embodiments, the 3' transposon insertion junction is amplified by a pair of primer comprising the nucleic acid sequence set forth in SEQ ID NO:14 (GGGCTAGTCGGTGTATCAT) and SEQ ID NO:11 (TT-GCGGTACAAGACCAAAGA).

According to yet further embodiments, the pair of primers is designed to amplify the 5' genomic junction of the transposon insertion within the Psy1 allele. According to certain exemplary embodiments, the 5' transposon insertion junction is amplified by a pair of primer comprising the nucleic acid sequence set forth in SEQ ID NO:15 (CTG-GAAGGGTGACCGATAAA) and SEQ ID NO:16 (ATGA-TACACCGACTAGCCC).

According to another aspect, the present invention provide a method for producing a tomato cultivar producing fruit having an Arlecchino phenotype of yellow-red segments spanning from the placenta and/or locules across the fruit pericarp to the epidermis, the method comprises mutating at least one allele of Phytoene synthase 1 with an insertion mutation. According to certain embodiments, the insertion is within an intron resulting in a non-functional Psy1 allele. According to additional exemplary embodiments, the insertion is within intron No. 8 located between exon 8 and exon 9 of the Psy1 gene having the nucleic acid sequence set forth in SEQ ID NO:6, resulting in Psy1 splice variants encoding non function protein.

According to yet additional aspect, the present invention provides an isolated polynucleotide encoding a mutated Phytoene synthase 1 comprising the nucleic acids sequence as set forth in SEQ ID NO:5.

Other objects, features and advantages of the present invention will become clear from the following description and drawings.

BRIEF DESCRIPTION OF THE FIGURES

FIG. 5 demonstrates the nucleotide sequence differences in the transposon insertion/excision site within the Psy1 gene in red and yellow sections of Arlecchino fruit. Yellow sections were homozygous for the flanking repeats whereas red sections were heterozygous to this sequence because the transposon was excised from one allele.

FIG. 7 is a schematic demonstration of the transposon and flanked nucleic acid insertion within the Psy1 gene (FIG. 7A) and of the amplified Arlecchino marker (FIG. 7B).

FIG. 8 shows the nucleic acids sequence of the r$^{ar1}$ allele (SEQ ID NO:5). Upper case letters indicate sequences of tomato wild type Psy1 gene, with exons marked in bold letters. Small case letters indicate the Arlecchino intron sequence and the flanked nucleotide insertion is boxed.

DETAILED DESCRIPTION OF THE INVENTION

Figure 1:
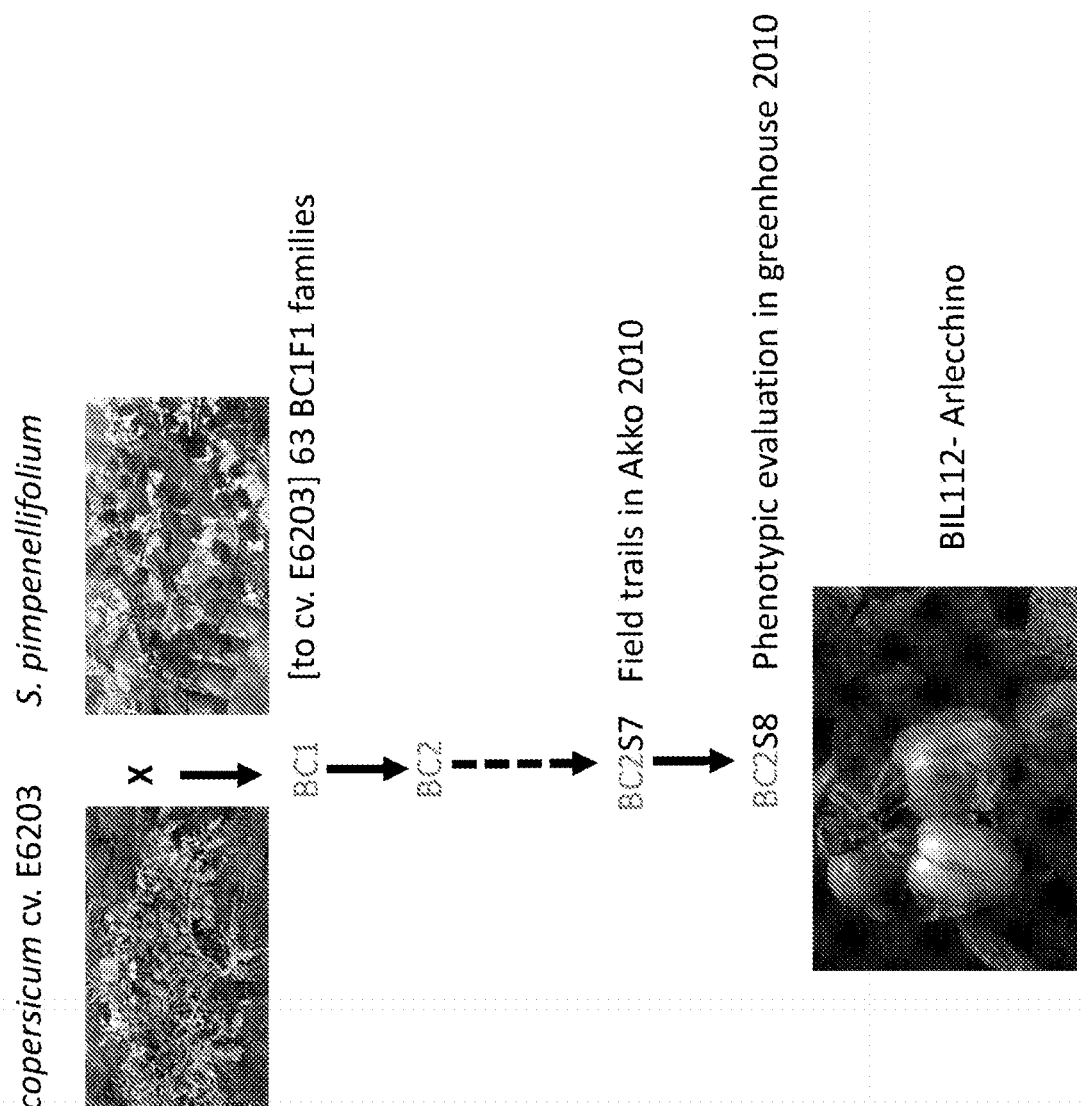
FIG. 1 shows the construction of the *Solanum pimpinellifolium* (Sp) LA1589 backcross inbred line (BIL) population and the production of the Arlecchino mutation detected only in a single plant in the BIL#112 family in the year 2010.

The present invention provides tomato cultivars producing fruit having the appealing appearance of red and yellow stripes or segments that span across all the edible part of the fruit—from the inner seed area and up to the most external layer of the exocarp (fruit skin), through the mesocrap and endocarp. The present invention further discloses for the first time the genetic configuration which is linked to this appearance, designated herein Arlecchino.

Definitions

The term "plant" is used herein in its broadest sense. It also refers to a plurality of plant cells that are largely differentiated into a structure that is present at any stage of a plant's development. Such structures include, but are not limited to, a root, stem, shoot, leaf, flower, petal, fruit, etc. As used herein, the term "plant part" typically refers to a part of a tomato plant, including single cells and cell tissues such as plant cells that are intact in plants, cell clumps and tissue cultures from which tomato plants can be regenerated. Examples of plant parts include, but are not limited to, single cells and tissues from pollen, ovules, leaves, embryos, roots, root tips, anthers, flowers, fruits, stems, shoots, and seeds; as well as pollen, ovules, leaves, embryos, roots, root tips, anthers, flowers, fruits, stems, shoots, scions, rootstocks, seeds, protoplasts, calli, and the like.

The term "pericarp" as is known in the art refers to the wall of a matured ovary. Specifically, tomato fruit pericarp refers to the fruit wall, which surrounds the seeds and placenta. The term "pericarp" includes the exocarp, mesocarp and endocarp as well as the radial pericarp.

The term "gene", as used herein, refers to a hereditary unit consisting of a sequence of DNA that occupies a specific location on a chromosome and that contains the genetic instruction for a particular characteristics or trait in an organism. The term "gene" thus refers to a nucleic acid (e.g., DNA or RNA) sequence that comprises coding sequences necessary for the production of RNA or a polypeptide or its precursor. A functional polypeptide can be encoded by a full-length coding sequence or by any part thereof as long as the desired activity or functional properties (for example, enzymatic activity, ligand binding, signal transduction, etc.) of the polypeptide are retained. The term "parts thereof" when used in reference to a gene refers to fragments of that gene. The fragments may range in size from a few nucleotides to the entire gene sequence minus one nucleotide.

Thus, "a nucleic acid sequence comprising at least a part of a gene" may comprise fragments of the gene or the entire gene. The term "gene" encompasses both cDNA and genomic forms of a gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences.

As sued herein, the term "allele" refers to alternative or a variant form of a gene or of any kind of identifiable genetic element, which are alternative in inheritance because they are situated at the same locus in homologous chromosomes. Such alternative or variant forms may be the result of single nucleotide polymorphisms, insertions, inversions, translocations or deletions, or the consequence of gene regulation caused by, for example, chemical or structural modification, transcription regulation or post-translational modification/regulation. In a diploid cell or organism, the two alleles of a given gene or genetic element typically occupy corresponding loci on a pair of homologous chromosomes.

As used herein, the terms "$r^{arl}$ allele" or "$r^{arl}$ allele of Psy1" are used herein interchangeably and refer to a Phytoene synthase 1 allele comprising an insertion within intron of the allele, wherein the insertion results in a non-functional splice variant of Psy1. According to certain exemplary embodiments, the terms refer to the nucleic acid sequence set forth in SEQ ID NO:5.

The term "genotype" as used herein refers to the genetic constitution of a cell or organism. As is known in the art, a genotype can relate to a single locus or to multiple loci, whether the loci are related or unrelated and/or are linked or unlinked. In some embodiments, an individual's genotype relates to one or more genes that are related in that the one or more of the genes are involved in the expression of a phenotype of interest (e.g. color trait as defined herein). Thus, in some embodiments a genotype comprises a summary of one or more alleles present within an individual at one or more genetic loci.

The term "phenotype" as used herein refers to the appearance or other detectable characteristic of an individual, in particular individual plant. According to certain embodiments, the phenotype results from the plant genotype. According to additional embodiments, the phenotype results from the interaction of its genome, proteome and/or metabolome with the environment.

The terms "segment", "section" and their plurality forms are used herein interchangeably and refer to area of the tomato fruit which is either yellow or red in color, forming the red-yellow phenotype of Arlecchino.

As used herein, the term "breeding", and grammatical variants thereof, refer to any process that generates a progeny individual. Breeding can be sexual or asexual, or any combination thereof. Exemplary non-limiting types of breeding include crossings, selfing, doubled haploid derivative generation, and combinations thereof.

As used herein the term "selfing" refers to a controlled self-pollination of a plant, i.e. contacting pollen and ovule produced by the same plant. The term "crossing" refers to controlled cross-pollination, i.e. contacting pollen and ovule each produced by a different plant.

The term "donor", as used herein, refers to the plant or plant line from which the trait, introgression or genomic segment originates, and which donor may have the trait, introgression or genomic segment either heterozygous or homozygous.

The term "recipient", as used herein, refers to the plant or plant line receiving the trait, introgression or genomic segment from a donor, and which recipient may or may not have the trait, introgression or genomic segment itself either heterozygous or homozygous.

The term "offspring" as used herein refers to any plant resulting as progeny from a vegetative or sexual reproduction from one or more parent plants or descendants thereof. For instance an offspring plant can be obtained by cloning or selfing of a parent plant or by crossing two parent plants and include selfing as well as the F1 or F2 or still further generations. An F1 is a first-generation offspring produced from parents at least one of which is used for the first time as donor of a trait, while offspring of second generation (F2) or subsequent generations (F3, F4, and the like) are specimens produced from selfing of F1 s, F2s and the like. An F1 can thus be (and in some embodiments is) a hybrid resulting from a cross between two true breeding parents (true-breeding is homozygous for a trait), while an F2 can be (and in some embodiments is) an offspring resulting from self-pollination of the F1 hybrids.

As used herein, the term "hybrid" refers to any offspring of a cross between two genetically unlike individuals, including but not limited to the cross between two inbred lines.

As used herein, the term "inbred" means a substantially homozygous individual plant or plant line.

As used herein, the term "backcross", and grammatical variants thereof, refers to a process in which a breeder crosses a hybrid progeny back to one of the parents, for example, a first generation hybrid F1 with one of the parental genotypes of the F1 hybrid. In some embodiments, a backcross is performed repeatedly, with a progeny individual of one backcross being itself backcrossed to the same parental genotype.

A "cultivated tomato plant" or "tomato cultivar" or "tomato cultivar plant" is understood within the scope of the invention to refer to a plant of the Solanaceae clade *Lycopersicon* that is no longer in the natural state but has been developed by human care and for human use and/or consumption. "Cultivated tomato plants" or "tomato cultivars" or tomato cultivar plants" are further understood to exclude those wild species which comprise the trait being subject of this invention as a natural trait and/or part of their natural genetics. Examples of tomatoes include *Solanum lycopersicum* (formally *Lycopersicon esculentum*), *Solanum cerasiforme, Solanum cheesmanii, Solanum chilense, Solanum chmielewskii, Solanum hirsuturn, Solanum parviflorum, Solanum pennellii, Solanum peruvianum*, or *Solanum lycopersicoides*. According to certain embodiments, the tomato cultivar is *Solanum lycopersicum* (taxonomy according to Peralta I et al. 2005 Northern Peru Systematic Botany 30(2):424-434.

The term "heterozygous" is used herein to refer to unlike alleles at one or more corresponding loci on homologous chromosomes.

The term "homozygous" is used herein to refer to like alleles at one or more corresponding loci on homologous chromosomes.

New appearances of tomato fruit that would be appealing to the customer are always desired. The sophisticated customer also requires that the fruit are firm, tasty, and have reasonable shelf live. The tomato grower is looking for a plant that is resistant to biotic and abiotic stress and produces high yield. Understanding the genetic inheritance rules in plants and the fast development of molecular genetics tools during the past decades facilitates the production of superior agricultural crops in general and tomato plants in particular.

Figure 2A:
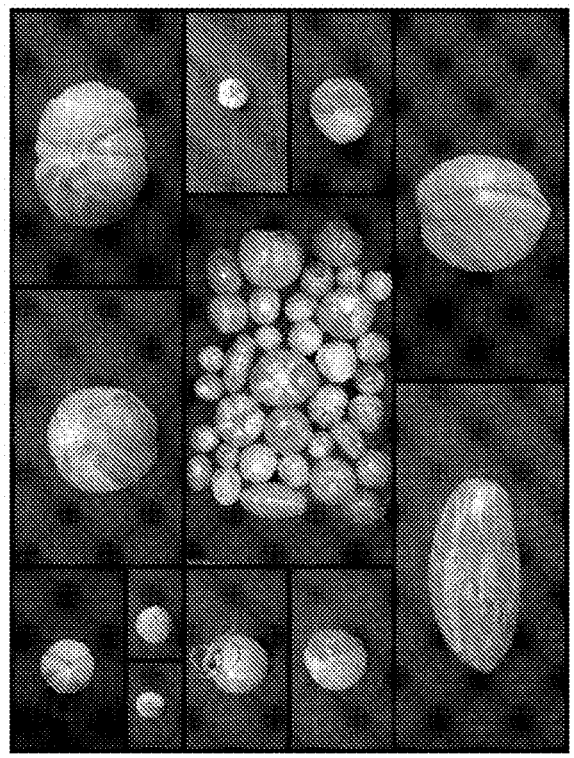
FIG. 2 shows the Arlecchino mutation phenotype in different genetic background showing whole fruit (A) and transverse sections (B).

In the course of studying the phenotype-genotype relationship in a population of tomato backcross inbred lines (BILs) produced on a background of a population with artificially induced mutations the inventors have unexpectedly produced a tomato plant having fruit with alternate yellow and red segments. This phenotype has been designated as "Arlecchino". In contrast to hitherto known fruit showing similar external fruit phenotype, the colored segments of Arlecchino were not restricted to the epidermis and/or outer layers of the fruit pericarp, but spanned from within the fruit (including the placenta and/or locules) across the pericarp and up to the most external epidermis layer (FIG. 2).

The color of the fruit as indicated herein refers to the color of ripening fruit at the breaker stage and up to a fully ripe or mature fruit. At the breaker stage there is a definite break of color from green to tannish-yellow, pink or red on the tomato fruit surface. The term "mature" as used herein means that the contents of two or more seed cavities have developed a jellylike consistency and the seeds are well developed. The Arlecchino phenotype is easily detected visually.

Tomato fruit is classified as a fleshy berry. As a true fruit, it develops from the ovary of the plant after fertilization. Tomato fruit can be either bilocular or multilocular. Most cultivated varieties except cherry tomatoes have two to five locules. The locules are surrounded by the pericarp. The pericarp includes the inner wall, columella; the radial wall, septa; and the outer wall (epidermis). The pericarp and the placenta comprise the fleshy tissue of the tomato. The seeds are located inside of the locular cavities and are enclosed in gelatinous membranes. There are vascular bundles throughout the outer wall of the pericarp and travelling from the stem to the center of the tomato and from there radiating to each seed.

The BILs population from which the Arlecchino mutated phenotype was isolated was constructed from a cross between the small red-fruited, self-compatible, wild accession of *Solanum pimpinellifolium* LA1589 and the *S. lycopersicum* processing-tomato, inbred variety, cv. E6203 (TA209). Without wishing to be bound by any specific theory or mechanism of action, the Arlecchino mutation may be the results of a "genomic shock" resulting from wide crosses.

One of the factors characterizing mutagens is that changes in the DNA are created via a variety of molecular mechanisms and thus the repertoire of the mutations obtained can vary dramatically among different mutagens (transitions, transversions, deletions or additions). Another known force that induces mutations results from the creation of interspecific populations by the crossing of evolutionary divergent types. Merging of divergent genomes can create a "genomic shock", a process described by McClintock (1984. Science 226:792-801). Despite intensive research, the molecular mechanisms that affect a genomic shock are not well characterized. However, it has been reported that the introgression of alien genomic segment into a divergent background can trigger genetic changes and mutations. This phenomenon has been previously described, a detailed work executed in wheat being an example (Shaked et al., 2001. Plant Cell 13:1749-1759). Shaked et al. have shown that upon the synthesis of new wheat allotetraploids events such as gene loss, gene silencing and activation are rather common. In wheat, interspecific hybridization followed by chromosome doubling leads to rapid, genetic and epigenetic changes, where retrotransposons appear to be the principal actors when their activity is activated by the genomic shock (Shaked et al., 2001, ibid; Ozkan et al., 2001. Plant Cell 13:1735-1747; Kashkush et al., 2003. Nat. Genet. 33:102-106).

Further breeding of the isolated Arlecchino-phenotype plant provided for the tomato plants of the present invention, which are cultivar tomato plants suitable for commercial growth.

The present invention further discloses the linkage between the Arlecchino phenotype and the presence of transposon insertion in at least one allele of the Phytoene synthase 1 (Psy1) gene. It is to be explicitly understood that the presence of the $r^{arl}$ allele is obligatory for the Arlecchino phenotype, but may not be the only factor responsible for its appearance.

Figure 8:
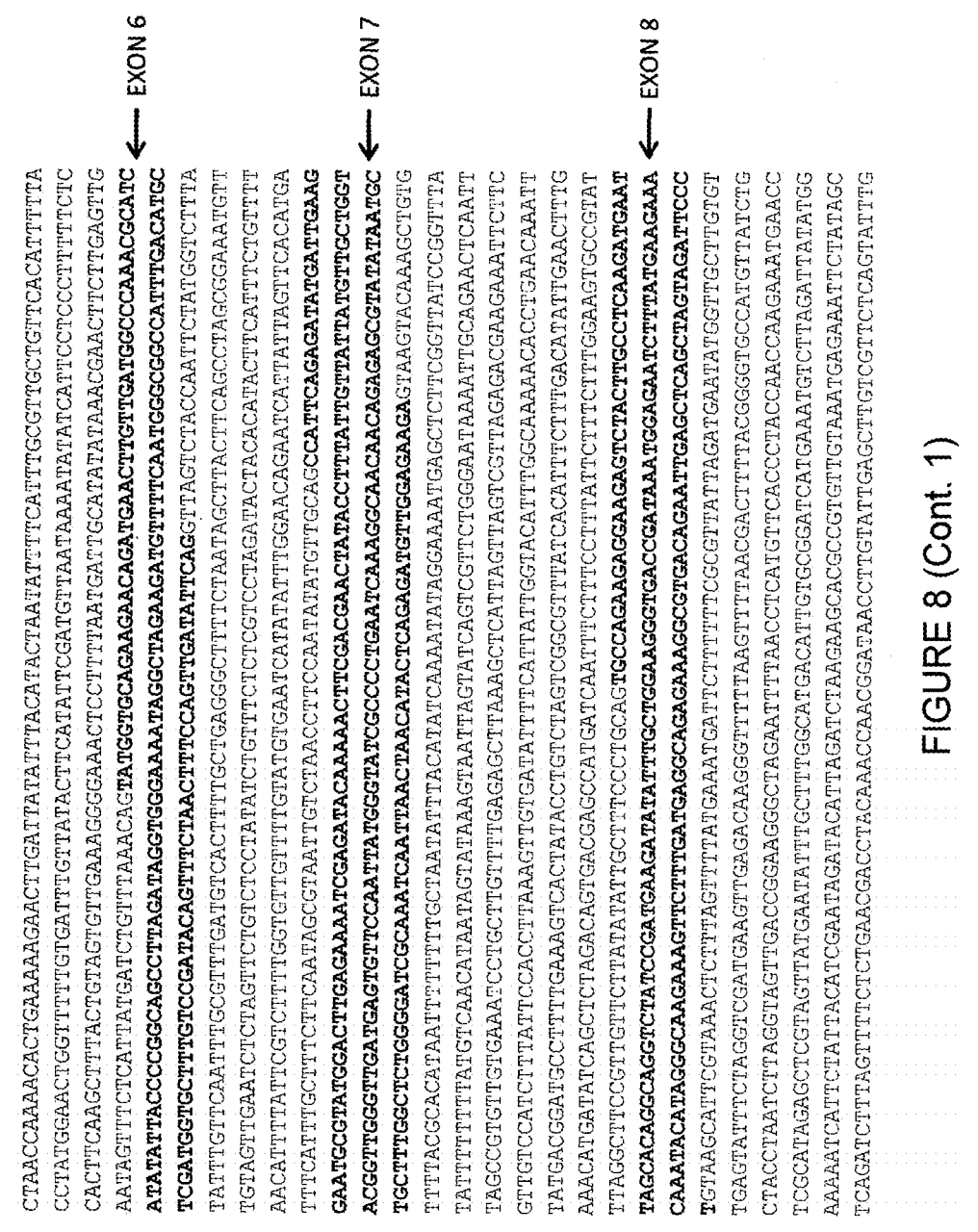

Sequencing the area of the initially observed insertion of the 9 base pairs (SEQ ID NO:1) within the Psy1 gene pointed to the presence of a direct repeat of the nucleic acid sequence TCTGGATA (SEQ ID NO:2). Insertion of transposons into a plant genome is typically characterized by the formation of sequence duplication in direct orientation at the place of insertion. As exemplified hereinbelow, the inventors of the present invention have discovered that the Arlecchino phenotype is indeed a result of transposon insertion in cells forming the fruit yellow sections. The insertion is within intron 8 of the Psy1 gene (according to the Psy1 sequence shown in FIG. 8) resulting in splice variants missing the last exon (exon 9) of Psy1 such that translation of a functional protein is impaired. The red sections cells comprise either wild type Psy1 alleles and/or cells in which the transposon has been excised without negatively affecting the gene transcription, enabling the translation of functional Phytoene synthase 1.

The present invention thus provides a tomato cultivar which produces fruit having an Arlecchino phenotype of yellow-red segments spanning from the placenta and/or locules across the fruit pericarp to the epidermis, wherein the phenotype is linked to at least one allele of $r^{arl}$, the $r^{arl}$ allele is Phytoene synthase 1 (Psy1) allele comprising an insertion within an intron of the allele, wherein the insertion results in a non-functional splice variant of Psy1.

According to certain embodiments, cells of the yellow segments of the Arlecchino fruit are homozygous for the $r^{arl}$ allele.

According to certain embodiments, the insertion comprises a transposon flanked by the nucleic acid sequence TCTGGATA (SEQ ID NO:2) at the transposon 3' end. According to additional embodiments, the insertion comprises a transposon flanked by the nucleic acid sequence ATCTGGATA (SEQ ID NO:1) at the transposon 3' end.

According to certain embodiments, the transposon belongs to the hAT family. According to some embodiments, the transposon comprises a nucleic acid sequence at least According to these embodiments, the transposon comprises a nucleic acids sequence at least 90%, 91%, 92%, 93%, 94%, 95%, 96%, 97%, 98%, 99% or 100% homologous to SEQ ID NO:3. Each possibility represents a separate embodiment of the present invention.

According to additional exemplary embodiments, the transposon consists of the nucleic acid sequence set forth in SEQ ID NO:3.

According to certain exemplary embodiments, the insertion within the Psy1 gene comprises a nucleic acid sequence at least 95%, at least 96%, at least 97%, at least 98%, at least 98% or at least 99% homologous to the nucleic acid sequence set forth in SEQ ID NO:4. According to certain exemplary embodiments, the insertion within the Psy1 gene comprises the nucleic acid sequence set forth in SEQ ID NO:4.

According to certain embodiments, the $r^{arl}$ allele of Psy1 comprises the nucleic acid sequence set forth in SEQ ID NO:5.

The present invention further provides methods for producing tomato cultivars having the Arlecchino phenotype, plants so produced and parts thereof.

According to a certain aspect, the present invention provides a method for producing a tomato cultivar producing fruit having an Arlecchino phenotype of yellow-red segments spanning from the placenta and/or locules across the fruit pericarp to the epidermis, the method comprising introducing into a tomato cultivar producing red fruit or a part thereof a genetic element comprising $r^{arl}$ allele of Phytoene synthase 1, the $r^{arl}$ allele comprises an insertion within an intron of the allele, wherein the insertion results in a non-functional splice variant of Psy1.

Introduction of the genetic element into the genome of a selected tomato cultivar can be performed using any method as is known in the art.

Plant breeders and in particular seed companies use elite breeding lines, generally referred to as "elite lines" to provide a constant quality product. The elite lines are the result of intensive inbreeding and combine multiple superior characteristics such as high yield, fruit quality, resistance to pests and diseases, and tolerance to abiotic stress. The average yield of these elite lines is generally much higher than the original wild accessions from which many of the modern tomato varieties are descendants. The elite lines can be used directly as crop plant, but are typically used to produce so-called F1 or single-cross hybrids, produced by a cross between two (homozygous or inbred) elite lines. The F1 hybrids thus combine the genetic properties of the two parents into a single plant. An additional benefit of hybrids is that they express hybrid vigor or heterosis, the phenomenon that hybrid plants grow better than either (inbred) parent and show higher yields.

Backcross or pedigree selection is one method by which breeders add desirable agronomic traits to their elite breeding lines. The method involves crossing the breeding line with a line that expresses the desirable trait followed by backcrossing offspring plants expressing the trait to the recurrent parent. As a result, the selection of an individual as a parent in a breeding program is based on the performance of its forebears. Such methods are most effective in breeding for qualitatively-inherited traits, i.e. traits which are present or absent.

Recurrent selection is an alternative breeding method for improving breeding lines and involves systematic testing and selection of desirable progeny followed by recombination of the selected individuals to form a new population. Recurrent selection has proven effective for improving quantitative traits in crop plants. Recurrent selection, however, decreases the rate of broadening genetic basis underlying the various traits in a breeding program, and its potential is therefore limited.

As disclosed herein, tomato plants producing yellow-red bicolor fruit can be produced by introducing a genetic element comprising $r^{arl}$ allele of Phytoene synthase 1, into an elite breeding line.

Introducing the $r^{arl}$ allele can be performed by plant breeding, i.e. by crossing a donor plant comprising the $r^{arl}$ allele with a recipient plant, preferably an elite cultivar tomato plant not comprising the $r^{arl}$ allele.

Alternatively, a nucleic acid, preferably DNA, comprising the $r^{arl}$ allele may be isolated by any method known in the art and introduced into the genome of a tomato plant producing red fruit.

Transforming plants with isolated nucleic acid sequence generally involves the construction of an expression vector that will function in plant cells. According to the teachings of the present invention, such a vector comprises a nucleic acid sequence that comprises the $r^{arl}$ allele. Typically, the vector comprises the $r^{arl}$ allele under control of or operatively linked to a regulatory element. According to certain embodiments, the regulatory element is selected from the group consisting of a promoter, an enhancer and a translation termination sequence. The expression vector may contain one or more such operably linked gene/alleles/regulatory element combinations, provided that at least one of the alleles contained in the combinations comprises the $r^{arl}$ allele. The vector(s) may be in the form of a plasmid, and can be used, alone or in combination with other plasmids, in a method for producing transgenic plants that produce fruit with the Arlecchino phenotype, using transformation methods known in the art to be suitable for transforming nucleic acid sequences into tomato (dicotyledonous) plants.

Expression vectors can include at least one marker (reporter) gene, operably linked to a regulatory element (such as a promoter) that allows transformed cells containing the marker to be either recovered by negative selection (by inhibiting the growth of cells that do not contain the selectable marker gene), or by positive selection (by screening for the product encoded by the markers gene). Many commonly used selectable marker genes for plant transformation are known in the art, and include, for example, genes that code for enzymes that metabolically detoxify a selective chemical agent which may be an antibiotic or a herbicide, or genes that encode an altered target which is insensitive to the inhibitor. Several positive selection methods are known in the art, such as mannose selection. Alternatively, marker-less transformation can be used to obtain plants without mentioned marker genes, the techniques for which are known in the art.

Methods for transforming a plant cell with nucleic acids sequences according to the present invention are known in the art. As used herein the term "transformation" or "transforming" describes a process by which a foreign nucleic acid sequence, such as a vector, enters and changes a recipient cell into a transformed, genetically modified or transgenic cell. Transformation may be stable, wherein the nucleic acid sequence is integrated into the plant genome and as such represents a stable and inherited trait, or transient, wherein the nucleic acid sequence is expressed by the cell transformed but is not integrated into the genome, and as such represents a transient trait. According to typical embodiments the nucleic acid sequence of the present invention is stably transformed into a plant cell.

There are various methods of introducing foreign genes into both monocotyledonous and dicotyledonous plants (for example, Potrykus I. 1991. Annu Rev Plant Physiol Plant Mol Biol 42:205-225; Shimamoto K et al., 1989. Nature 338:274-276).

The principal methods of the stable integration of exogenous DNA into plant genomic DNA includes two main approaches:

Agrobacterium-mediated gene transfer: The Agrobacterium-mediated system includes the use of plasmid vectors that contain defined DNA segments which integrate into the plant genomic DNA. Methods of inoculation of the plant tissue vary depending upon the plant species and the Agrobacterium delivery system. A widely used approach is the leaf-disc procedure, which can be performed with any tissue explant that provides a good source for initiation of whole-plant differentiation (Horsch et al., 1988. Plant Molecular Biology Manual A5, 1-9, Kluwer Academic Publishers, Dordrecht). A supplementary approach employs the Agrobacterium delivery system in combination with vacuum infiltration. Agrobacterium mediated transformation protocols for tomato plants are known to a person skilled in the art.

Direct nucleic acid transfer: There are various methods of direct nucleic acid transfer into plant cells. In electroporation, protoplasts are briefly exposed to a strong electric field, opening up mini-pores to allow DNA to enter. In microinjection, the nucleic acid is mechanically injected directly into the cells using micropipettes. In microparticle bombardment, the nucleic acid is adsorbed on microprojectiles such as magnesium sulfate crystals or tungsten particles, and the microprojectiles are physically accelerated into cells or plant tissues. Another method for introducing nucleic acids to plants is via the sonication of target cells. Alternatively, liposome or spheroplast fusion has been used to introduce expression vectors into plants.

Following transformation of tomato target tissues, expression of the above described selectable marker genes allows for preferential selection of transformed cells, tissues and/or plants, using regeneration and selection methods now well known in the art.

According to certain embodiments, the present invention provides a method for producing tomato plants with Arlecchino phenotype, comprising the steps of:
  (a) introducing a genetic element comprising the $r^{arl}$ allele from a donor tomato plant comprising the genetic element into a recipient tomato cultivar, preferably an elite cultivar to provide offspring cultivated tomato plants;
  (b) examining a nucleic acid sample obtained from each offspring cultivated tomato plants for the presence of $r^{arl}$ allele; and
  (c) selecting cultivated tomato plants comprising said $r^{arl}$ allele.

This method can be defined as "marker assisted selection" as the selection of the desired Arlecchino phenotype is performed using nucleic acid markers specific for the Arlecchino genotype. Since the Arlecchino phenotype can only be properly identified phenotypically when the plant has produced fruit, it is of particular advantage that the establishment of proper introgression of the genetic element in offspring plants may be monitored by using the gene specific markers.

Introducing the genetic element comprising the $r^{arl}$ allele of Psy1 into a recipient plant can be performed by any method as described hereinabove and is known in the art.

Any method for obtaining a genetic material from the offspring tomato cultivar and any suitable molecular marker as are known in the art can be used for selecting Arlecchino genotype according to the teachings of the present invention.

As used herein, the terms "molecular marker" or "molecular markers" refer to a molecular indicator that is used in methods for visualizing differences in characteristics of nucleic acid sequences. Examples of such indicators are diversity array technology (DArT) markers, restriction fragment length polymorphism (RFLP) markers, amplified fragment length polymorphism (AFLP) markers, single nucleotide polymorphisms (SNPs), sequence-characterized amplified regions (SCARs), cleaved amplified polymorphic sequence (CAPS) markers, sequence-characterized hybridization markers; or any combination thereof. According to certain exemplary embodiments, the step of examining a nucleic acid sample obtained from each offspring cultivated tomato plants for the presence of $r^{arl}$ allele comprise the use of a set of bi-directional primers. Bi-directional means that the orientation of the primers is such that one functions as the forward and one as the reverse primer in an amplification reaction of nucleic acid. The bi-directional primers are typically used in an amplification reaction on genomic DNA that amplifies a unique nucleic acid sequence of the $r^{arl}$ allele of Psy1 or a marker thereof but that does not amplify the wild type Psy1 allele. According to certain embodiments, the pair of primers is designed to amplify an $r^{arl}$ allele marker comprising the nucleic acid sequence set forth in SEQ ID NO:7 (TCTGGATAATCTGGATA).

According to certain exemplary embodiments, the $r^{arl}$ allele marker is amplified by a pair of primer comprising the nucleic acid sequence set forth in SEQ ID NO:10 (CAGTGCCAGAAGAGGAAGA) and SEQ ID NO:11 (TTGCGGTACAAGACCAAAGA).

According to additional embodiments, the pair of primers is designed to amplify the full length transposon insertion. According to certain exemplary embodiments, the transposon is amplified by a pair of primer comprising the nucleic acid sequence set forth in SEQ ID NO:12 (GTGGATCCTGAAATGGCTTG) and SEQ ID NO:13 (AGTACTAATAAAATGGTTTTGCC).

According to yet additional embodiments, the pair of primers is designed to amplify the 3' genomic junction of the transposon insertion within the Psy1 allele. According to certain exemplary embodiments, the 3' transposon insertion junction is amplified by a pair of primer comprising the nucleic acid sequence set forth in SEQ ID NO:14 (GGGCTAGTCGGTGTATCAT) and SEQ ID NO:11 (TTGCGGTACAAGACCAAAGA).

According to yet further embodiments, the pair of primers is designed to amplify the 5' genomic junction of the transposon insertion within the Psy1 allele. According to certain exemplary embodiments, the 5' transposon insertion junction is amplified by a pair of primer comprising the nucleic acid sequence set forth in SEQ ID NO:15 (CTGGAAGGGTGACCGATAAA) and SEQ ID NO:16 (ATGATACACCGACTAGCCC).

Additionally or alternatively, the markers are sequence specific probes that specifically hybridize under stringent conditions to the $r^{arl}$ allele of Psy1 but not to its wild type allele, and that can be detected thereafter by various methods as are well to a person skilled in the art.

Nevertheless, it is to be explicitly understood that the method aspects of the invention are not limited to the use of the markers identified herein, and that methods of the present invention may also make use of markers not explicitly disclosed herein or even yet to be identified, as identifying and using such markers is well within the skills of a person with knowledge in the Art.

In an additional or alternative method, the offspring cultivated tomato plants are phenotypically examined for the Arlecchino appearance as exemplifies hereinbelow. According to these embodiments, the offspring plants are grown to produce fruit and the fruit are examined for the presence of red and yellow sections throughout the fruit (the Arlecchino phenotype).

According to certain embodiments, the cultivar tomato plant having fruit with Arlecchino phenotype is an inbred plant. According to other embodiments, the cultivar tomato plant having fruit with Arlecchino phenotype is a hybrid plant. The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

Examples

Example 1: Whole Genome Backcross Inbred Lines (BILs)

The *Solanum pimpinellifolium* BILs were constructed from a cross between a small red-fruited self-compatible accession of the wild species *Solanum pimpinellifolium* (designated LA1589) and the processing-tomato, inbred variety, cv. E6203 (TA209) (*S. lycopersicum*) (Grandillo S and Tanksley S D. 1996. Theor. Appl. Genet. 92: 935-951). During the construction of BIL from both species, early generations were evaluated for yield associated traits, as a part of the advanced backcross (AB) QTL studies (reviewed by Grandillo S et al., 2007. Theor. Appl. Genet. 92: 935-951) and also for various morphological traits and biochemical properties. The *S. pimpinellifolium* BILs are composed from 178 lines and the genetic map of this resource was constructed from 4008, genome anchored, SNP markers that were found to be polymorphic between the wild species *S. pimpinellifolium* and the recurrent parent cv. E6203. The markers were divided into 873 bins with an average length of 0.87 Mbp/bin and composed an average of 4.59 SNPs/bin. Each of the bins showed a unique pattern of segregation, enabling the calculation of map distance in cM between pairs of neighboring bins. The calculated map is 1174.1 cM long and covers 100% of the wild species genome where the longest linkage group represents chromosome 3 (129.5 cM) and the shortest represents chromosome 6 (60.2 cM).

Example 2: The Arlecchino Mutation

The creation of the interspecific BIL population from *Solanum pimpinellifolium* and *Solanum lycopersicum* resulted in de novo formation of mutations within the BIL population. A single plant having an unstable fruit color phenotype was identified in BIL#112. The plant was produced during the year of 2010 (within the BC2self10 generation, FIG. 1 and the observed phenotype has not been detected previously in the various variety collections.

Figure 2B:
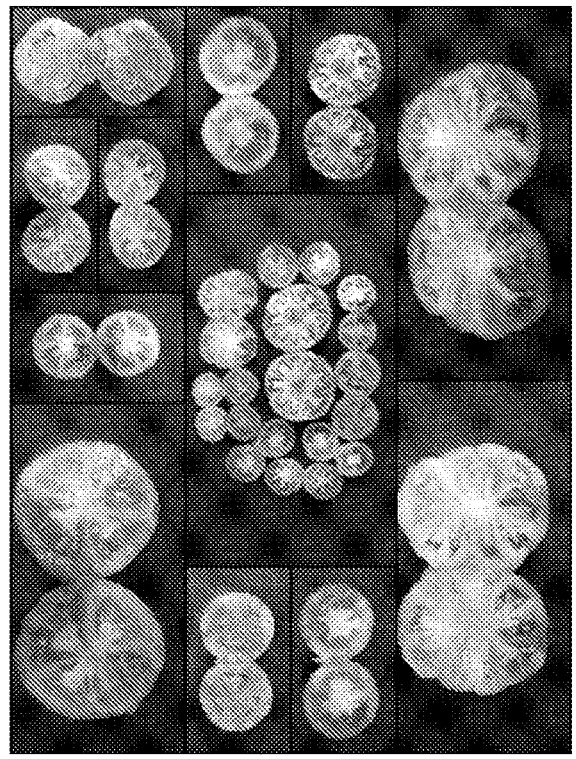

This unique mutant was characterized by parallel color bands of yellow and red, which paint the fruit longitudinally on the external epidermis (FIG. 2A) but importantly extends into the flesh (pericarp), seeds jelly and placenta (FIG. 2B). Hitherto, many mutations resulting in yellow tomato fruit have been identified; however, none of the mutations show yellow-red stripes or segments throughout the fruit cross, disclosed herein for the first time. Another characteristic of this mutant is that there is no observable phenotypic effect on fruit epidermis color in the immature green stage and only upon maturity the phenotype is revealed. The mutation phenotype has been assigned the name "Arlecchino". The first Arlecchino phenotype discovered in 2010 was unstable along the plant and the inflorescence, particularly in that complete red fruit were observed together with Arlecchino fruit on the same plant.

Figure 3:
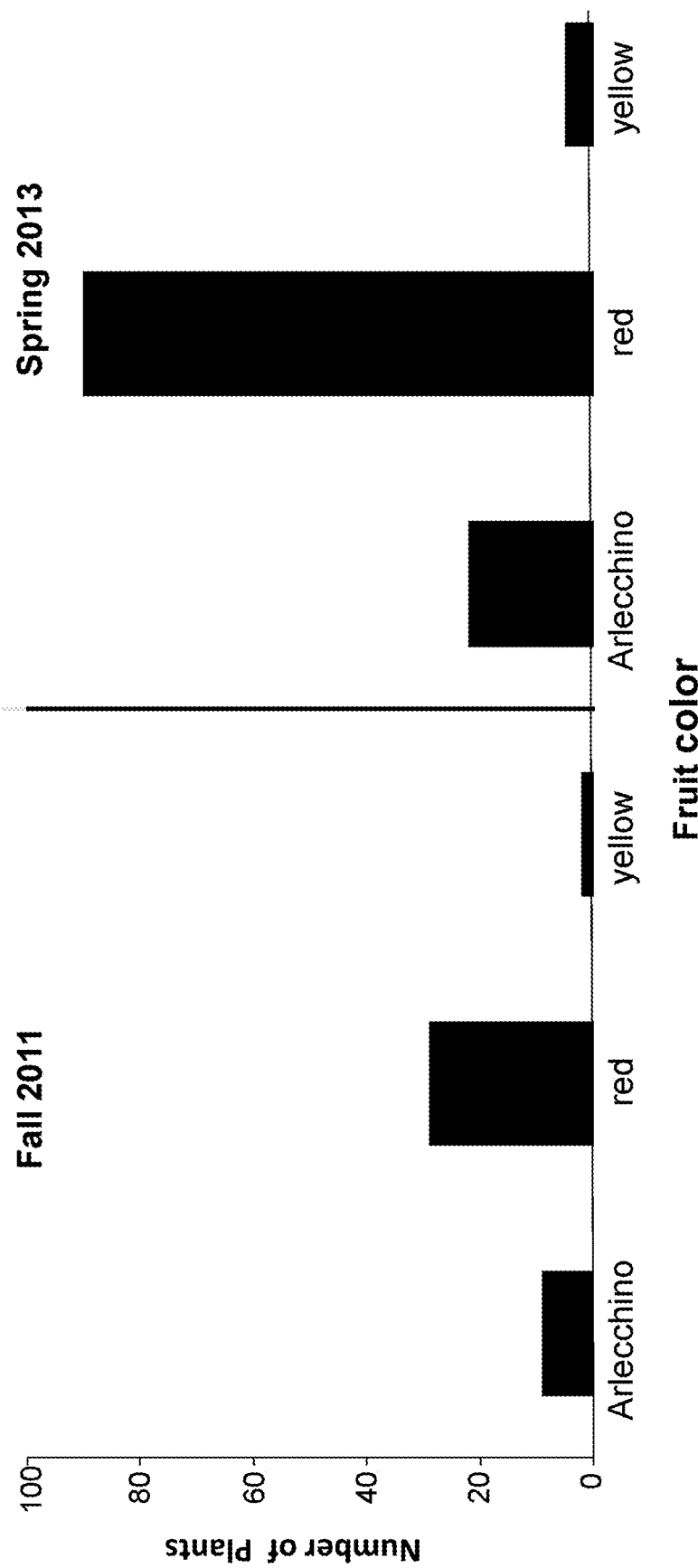
FIG. 3 demonstrates the segregation of fruit color traits in two independent F2 populations resulting from crosses of BIL#112 showing the Arlecchino phenotype and wild type red tomato lines.

The mode of inheritance of the Arlecchino phenotype was examined by crossing the plant identified in the BIL #112 with its parent cv. E6203 (TA209) and other wild type *Solanum lycopersicum* cultivars as compared to self-cross. The F1 hybrid plants had only normal red fruit while the BIL #112 self-progeny showed the characteristic Arlecchino phenotype. These results indicate that the new mutation is recessive. In the F2 population derived from selfing the F1 hybrid, the following progeny was observed: 29 plants with red fruits; 9 plants with the Arlecchino phenotype; and 2 plants with completely yellow fruit (Total 40). Additional F2 population derived from an independent F1 hybrid produced 90 plants with complete red fruit; 22 with Arlecchino fruit; and 5 with complete yellow fruit (total of 117 plants) (FIG. 3). The number of Arlecchino+yellow out of the total population fits the 1:3 ratio suggesting a single Mendelian gene with variable penetrance and expressivity.

To further examine the mode of the trait segregation, F3 progeny was examined. The F3 progeny was formed from selfing 31 F2 plants having red (21 plants), Arlecchino (8 plants) and yellow (2 plants) fruit phenotype. About 40 plants of the F3 generation of each F2 cross (31×40) were examined. The plants were phenotyped for fruit color and the genotype of the F2 plant was derived based on the progeny tested. The results indicate that 13 plants out of 21 red F2 plants segregated for the fruit phenotype at a ratio of 25% Arlecchino and 75% red (Table 1). The other eight red fruit F2 plants did not segregate in their F3 progeny meaning that all the F3 plants were red (the F3 of Plant 4853-26 showed only a single Arlecchino phenotype and thus it was assumed to be a contaminant and therefore this line was scored as homozygous; Table 1). The two yellow-phenotype F2 plants did not segregate and all the F3 progeny plants had completely yellow fruits. The 8 Arlecchino F2 plant did not show any consistent segregation ratio. All F3 progeny of line No. 4853-27 showed the Arlecchino phenotype, indicating this line as a stable Arlecchino parent.

TABLE 1

Summary of F3 Progeny Tests

| Line | F2 Phenotype (Fruit Color) | Red | Arlecchino | Yellow | Total | Estimated genotype |
|---|---|---|---|---|---|---|
| 4583-1 | Red | 33 | 7 | 0 | 40 | Heterozygous |
| 4583-2 | Arlecchino | 14 | 16 | 0 | 30 | |
| 4583-3 | Red | 15 | 0 | 0 | 15 | Homozygous |
| 4583-4 | Red | 40 | 0 | 0 | 40 | Homozygous |
| 4583-5 | Arlecchino | 22 | 7 | 0 | 29 | |
| 45836 | Red | 28 | 8 | 0 | 36 | Heterozygous |
| 4583-7 | Red | 37 | 0 | 0 | 37 | Homozygous |
| 4583-8 | Red | 26 | 6 | 0 | 32 | Heterozygous |
| 4583-9 | Red | 22 | 0 | 0 | 22 | Homozygous |
| 4583-10 | Red | 30 | 9 | 0 | 39 | Heterozygous |
| 4583-11 | Red | 40 | 0 | 0 | 40 | Homozygous |
| 4583-12 | Red | 32 | 8 | 0 | 40 | Heterozygous |
| 4583-13 | Red | 14 | 7 | 0 | 21 | Heterozygous |
| 4583-14 | Red | 34 | 6 | 0 | 40 | Heterozygous |
| 4583-15 | Yellow | 0 | 0 | 40 | 40 | |
| 4583-16 | Red | 30 | 10 | 0 | 40 | Heterozygous |
| 4583-17 | Arlecchino | 19 | 13 | 0 | 32 | |
| 4583-18 | Red | 40 | 0 | 0 | 40 | Homozygous |
| 4583-19 | Red | 36 | 4 | 0 | 40 | Heterozygous |
| 4583-20 | Red | 22 | 8 | 0 | 30 | Heterozygous |
| 4583-21 | Red | 25 | 0 | 0 | 25 | Homozygous |

TABLE 1-continued

Summary of F3 Progeny Tests

| Line | F2 Phenotype (Fruit Color) | F3 Phenotype (Fruit Color) | | | | Estimated genotype |
|---|---|---|---|---|---|---|
| | | Red | Arlecchino | Yellow | Total | |
| 4583-22 | Arlecchino | 14 | 21 | 0 | 35 | |
| 4583-23 | Red | | | | | |
| 4583-24 | Red | 12 | 4 | 0 | 16 | Heterozygous |
| 4583-25 | Yellow | 0 | 0 | 35 | 35 | |
| 4583-26 | Red | 32 | 1* | 0 | 32 | Homozygous |
| 4583-27 | Arlecchino | 0 | 16 | 0 | 16 | |
| 4583-28 | Arlecchino | 5 | 26 | 0 | 31 | |
| 4583-29 | Red | 19 | 6 | 0 | 25 | Heterozygous |
| 4583-30 | Red | | | | | |
| 4583-31 | Red | 24 | 11 | 0 | 35 | Heterozygous |
| 4583-32 | Red | | | | | |
| 4583-33 | Red | | | | | |
| 4583-34 | Arlecchino | 21 | 9 | 0 | 30 | |
| 4583-35 | Arlecchino | 32 | 8 | 0 | 40 | |
| 4583-36 | Red | | | | | |
| 4583-37 | Red | | | | | |
| 4583-38 | Red | | | | | |
| 4583-39 | Arlecchino | | | | | |
| 4583-40 | Red | | | | | |

Example 3: Allelic Configuration of the Arlecchino Phenotype

The results described above indicated that the Arlecchino phenotype is recessively inherited as fruit of F1 plants derived from the cross of BIL#112 and TA209 and other wild type (WT) cultivars were found to be completely red. Phenotypic complementation was also found in F1 plants derived from crosses of BIL#112 to the tangerine mutation e3406m2 and the zeta mutation e2083m1. Only in crosses of plant having the Arlecchino phenotype two independent mutations having the phenotype yellow flesh (r/r; defective in the Phytoene synthase 1 gene (Psy1) showed lack of complementation and the fruit showed a mild stripped phenotype (Table 2). These results suggest that Arlecchino is possibly allelic to yellow flesh.

TABLE 2

Allelism tests of the Arlecchino phenotype

| Line | E6203 (TA209) (R/R) | M82 (R/R) | e3756m2 (r/r) | LA2997 (r/r) | e3406m2 (t/t) | e2083m1 (zeta/zeta) |
|---|---|---|---|---|---|---|
| BIL 112 Arlecchino | Red | Red | Weak Arlecchino | Weak Arlecchino | Red | Red |

Example 4: Analysis of Carotenoid Content in Arlecchino-Phenotype Fruit

Figure 4:
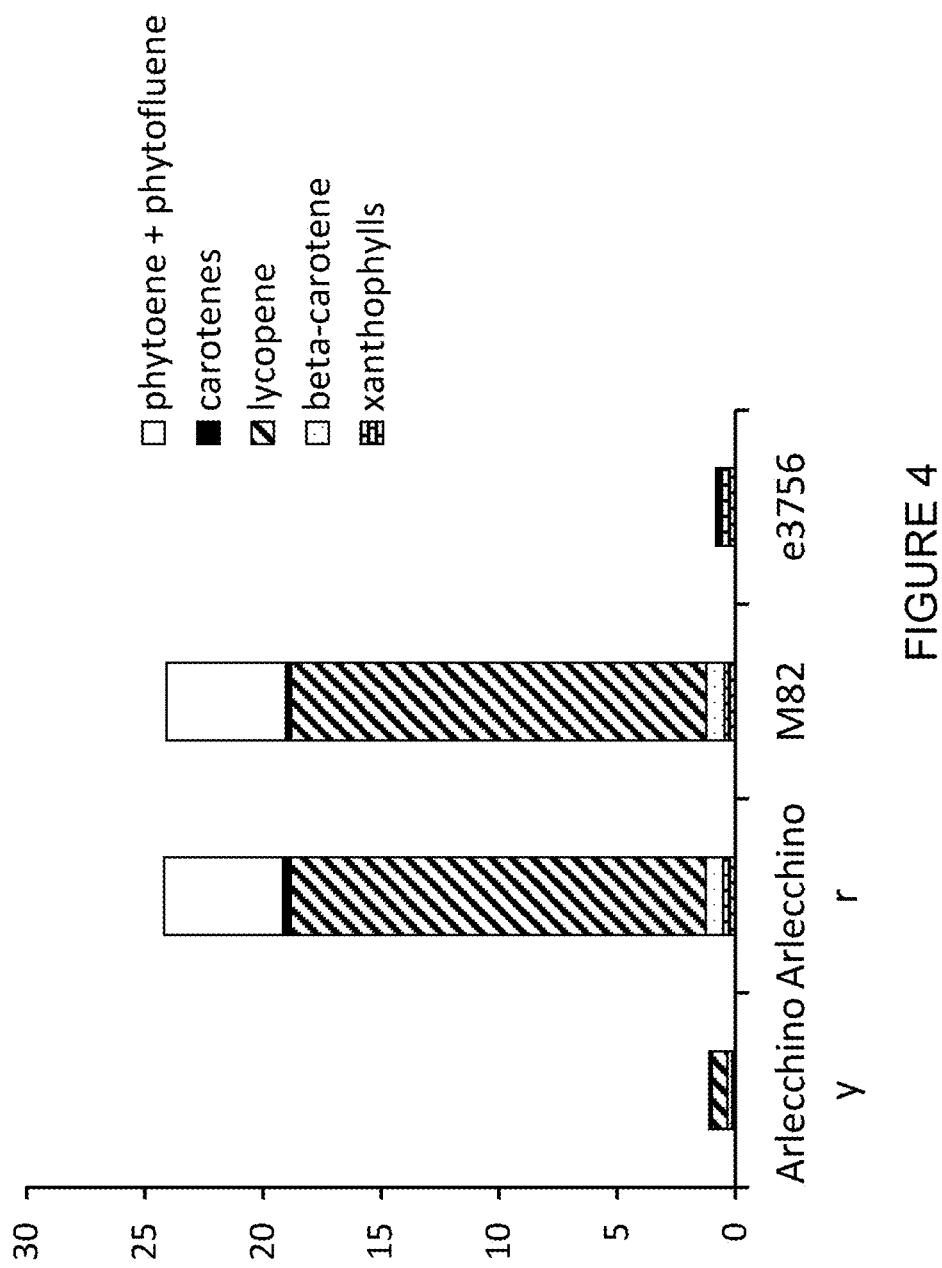
FIG. 4 shows the carotenoid concentration (μg/g Fresh Weight) in fruit samples of red (r) and yellow (y) sectors of Arlecchino compared with wild type (M82) and the yellow-flesh mutant r3756.

The carotenoid content within the red and yellow sections of ripe fruit having Arlecchino phenotype was examined and compared to the carotenoid content within red fruit of wild type tomato (M82) and yellow fruit of the yellow flesh variety e3756m2 (r/r; M82 EMS derivative). The carotenoids were extracted from the different section as described in Kachanovsky et al. (Kachanovsky D E et al., 2012. Proc. Natl. Acad. Sci. 109:19021-19026) and separated using high performance liquid chromatography (HPLC) using Waters 996 photodiode array detector (Ronen G et. al., 1999. Plant J 17:341-351). Red sections within the Arlecchino fruit have about 5 times higher total carotenoid content with a profile similar to wild type fruit while the yellow sections carotenoid content is significantly lower with a profile similar to the yellow flesh (e3756m2) mutant fruit (FIG. 4, Table 3).

TABLE 3

Carotenoid composition in red and yellow sections of ripe Arlecchino fruit (µg/g fresh weight)

| | Arlecchino Red section | Arlecchino Yellow sections |
|---|---|---|
| Phytoene | 6.57 ± 2.42 | 0.19 ± 0.04 |
| phytofluene | 4.13 ± 1.96 | 0.14 ± 0.05 |
| trans-Lycopene | 7.96 ± 7.18 | 1.46 ± 0.88 |
| β-Carotene | 2.79 ± 1.06 | 0.29 ± 0.99 |
| Lutein | 1.13 ± 0.30 | 0.76 ± 0.15 |
| tri-cis-ζ-carotene | 0.40 ± 0.20 | — |
| di-cis-ζ-carotene | 0.42 ± 0.20 | — |
| Others | 1.53 ± 1.07 | 1.14 ± 0.24 |
| Total carotenoids | 26.7 ± 4.42 | 5.24 ± 2.38 |

Example 5: Sequence Analysis of the Arlecchino-Phenotype Mutation

Carotenoids are 40-carbon isoprenoid pigments synthesized by all plants, algae and cyanobacteria as well as by several non-photosynthetic bacteria and fungi. The polyene chain of carotenoids may extend from 3 to 15 conjugated double bonds, which are responsible for the carotenoid characteristic absorption spectra and confer specific photochemical properties. The first committed step in the carotenoid pathway is the head to head condensation of two geranylgeranyl pyrophosphate (GGPP) molecules to produce phytoene, the first C40 carotenoid, catalyzed by the enzyme phytoene synthase (PSY). Initial DNA sequencing of Phytoene synthase 1 in the original BIL#112 Arlecchino phenotype plant revealed a 9 bp insertion in intron 8 (ATCTGGATA, SEQ ID NO:1) that was inserted after nucleotide 3338.

Initial Sequence Analysis of Intron Eight in Yellow and Red Sections of Arlecchino Fruit Intron eight of Psy1 was amplified by PCR from DNA samples obtained from red and yellow sections of fruit of Arlecchino phenotype and cloned into pGEM plasmid vector. Genomic DNA was extracted using a Genomic Plant DNA Purification Kit (Thermo). The intron was amplified using the primers listed in Table 4 below. E. coli cells were tranfected with pGEM plasmids carrying PCR products from yellow sectors or from red sectors. Seven E. coli colonies with pGEm clones from yellow tissue and 21 colonies with pGEM clones from the red tissues were tested. All DNA clones from yellow tissue showed the same sequence pattern of a duplication of the direct repeats of TCTGGATA (SEQ ID NO:2) separated by Adenine ("A") nucleotide (SEQ ID NO:7) designated herein as "the Arlecchino marker". The clones from the red tissues showed sequence variability amongst the colonies, with majority of the colonies containing transposon excision footprints while the rest of the colonies showing the same pattern as observed in the yellow colonies (FIG. 5). These results indicated a possibility of an excision of a transposon from one copy or by contamination of yellow cells in the red section.

TABLE 4

Primer pair for detecting the Arlecchino marker

| Primer designation | Sequence | SEQ ID NO. |
|---|---|---|
| Primer ARL4 forward | 5'-CAGTGCCAGAAGAGGAAGA-3' | 10 |
| Primer ARL4 reveres | 5'-TTGCGGTACAAGACCAAAGA-3' | 11 |

Determining the Complete Sequence of the $r^{arl}$ Allele

Initial PCR analysis confirmed the presence of the Arlecchino marker. PCR was conducted using READYMIX kit (Syntezza), 50-100 ng of genomic DNA, 0.4 µM of the Forward and Reverse primers listed in Table 4 hereinabove. PCR was initiated using a denaturation step at 95° C. for 2 min, followed by 38 cycles of 45 s denaturation at 96° C., 30 s annealing at 58-60° C., and 90 s extension at 72° C., and finally 10 m extension at 72° C.

To sequence the full length of Psy1 transcript from Arlecchino red and yellow fruits sections, 3'RACE was executed. RNA was extracted from yellow and red sectors of Arlecchino fruits by Thermo scientific GeneJET plant RNA purification Mini Kit #K0801. RNA was treated with Dnase I (New England BioLabs #M0303L) and then reverse transcribed by M-Mulv Reverse Transctiptase (New Englands BioLabs #M0253L) using an Oligo-dT-adaptor primer.

To amplify the Psy1 transcripts a PCR reaction was performed using a specific primer for Psy1 and an adaptor primer (Table 5).

TABLE 5

Primers used in 3'RACE assay

| Primer description | Sequence | SEQ ID NO. |
|---|---|---|
| Oligo-dT-adaptor primer | ctgtgaatgctgcgactacgatT(X20) | 17 |
| Adaptor primer | ctgtgaatgctgcgactacgat | 18 |
| Psy1 specific primer | AACTTGTTGATGGCCCAAAC | 19 |

Amplified Psy1 transcripts were cloned into pJET library (Thermo Scientific CloneJET PCR Cloning Kit).

Figure 6:
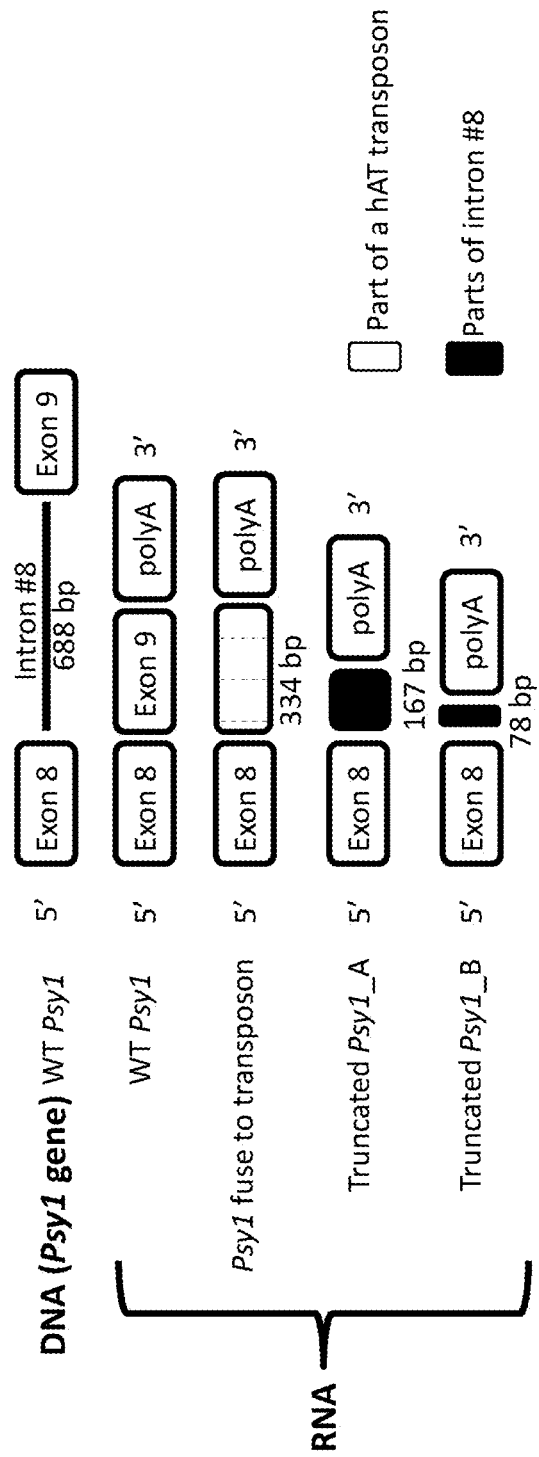
FIG. 6 is a schematic demonstration of the amplified segments of Psy1 transcripts obtained from different color sections of Arlecchino fruit.

Three spliced variants were detected in colonies obtained from Arlecchino fruit yellow sections, while in colonies obtained from red sections wild type transcript of Psy1 was detected in addition to the mutated transcripts. Two of the transcripts were found to be fused to a short part from the last intron and the third transcript was found to be fused to 400 bp sequence of a known hAT super-family transposon. In all three variants, the last exon (exon 9) was missing (FIG. 6).

Based on the above analysis, several primer pairs were designed (Table 6). Genomic DNA was extracted from young leaves or yellow fruit sections of plants having the Arlecchino phenotype using a Genomic Plant DNA Purification Kit (Thermo). PCR was conducted using a 50 ng-100 ng of genomic DNA, PCR buffer, 2.5 mM dNTPs, 0.2 µM-0.3 µM of the Forward and Reverse primers, and 0.5 units of PrimeSTAR GXL DNA Polymerase (Takara Bio). PCR was initiated using a denaturation step at 98° C. for 3 min, followed by 38 cycles of 10 seconds denaturation at 96° C., 15 seconds annealing at 55-60° C., and 180 seconds extension at 68° C., and finally 90 seconds extension at 68° C. These reactions enabled the amplification of the full length transposon as well of the area of the Psy1 adjacent to the intron, as described in FIG. 8.

TABLE 6

Primer pairs for detecting the $r^{arl}$ allele

| Primer designation | Sequence | SEQ ID NO. | Purpose |
|---|---|---|---|
| Primer ARL1 Forward | 5'-GTGGATCCTGAAATGGCTTG-3 | 12 | Amplification of full length of transposon |
| Primer ARL1 Reverse | 5'-AGTACTAATAAAATGGTTTTGCC-3' | 13 | |
| Primer ARL2 Forward | 5'-GGGCTAGTCGGTGTATCAT-3' | 14 | Amplification of 3'genomic junctions of the transposon |
| Primer ARL2 Reverse | 5'-TTGCGGTACAAGACCAAAGA-3' | 11 | |
| Primer ARL3 Forward | 5'-CTGGAAGGGTGACCGATAAA-3' | 15 | Amplification of 5'genomic junctions of the transposon |
| Primer ARL3 Reverse | 5'-ATGATACACCGACTAGCCC-3' | 16 | |

Example 6: Sequence Analysis of Psy1 Transcript in Leaves and Fruit Yellow and Red Sections of Arlecchino Plants Psy1 transcript was amplified from RNA extracted from Arlecchino red and yellow fruit sections and Arlecchino leaf tissue using three pairs of primers. Reaction I, aimed at amplifying a segment stretching from exon 7 to exon 8 was successful in all three RNA samples examined. Reaction II and III, aimed at amplifying of a segment stretching from exon 7 to exon 9 and from exon 8 to exon 9, respectively, were successful only in samples containing RNA extracted from Arlecchino fruit red sections (Table 7). These results indicate that exon 9 is impaired in yellow and leaf tissue.

TABLE 7

Amplification of Psy1 transcript using three different primer pairs

| Reaction | Forward primers: | Reverse primers: | Area amplified |
|---|---|---|---|
| I | Psy1_f2 AGCCATTCAGAGATATGATTGA (SEQ ID NO: 20) | Psy1-4 rev ATCGGATAGACCTGCCTGTG (SEQ ID NO: 21) | Exon #7-Exon #8 |
| II | psy1_f2 AGCCATTCAGAGATATGATTGA (SEQ ID NO: 20) | Psy1_r2 TTATCITTGAAGAGAGGCAGT (SEQ ID NO: 22) | Exon #7-Exon #9 |
| III | ARL3 CTGGAAGGGTGACCGATAAA (SEQ ID NO: 15) | Psy1_r3 GATAAAGTGAAGATACAACAAC (SEQ ID NO: 23) | Exon #8-Exon #9 |

Example 7: The Arlecchino Transposon

Arlecchino transposon sequence was completed using the GXL polymerase and primers:

```
                                          (SEQ ID NO: 12)
    ARL1 Forward: GTGGATCCTGAAATGGCTTG;

(SEQ ID NO: 13)
    ARL1 Reveres: AGTACTAATAAAATGGTTTTGCC;
    and (SEQ ID NO: 16)
    ARL3 Reveres: ATGATACACCGACTAGCCC.
```

The transposon comprises 3903 nucleic acids (SEQ ID NO:3) and with inverted repeats at the 5' and 3' ends providing for its insertion into Psy1 (FIG. 7).

Sequencing of the Arlecchino transposon showed that it contains an open reading frame similar to known transposases (such as in Tam3 from *Antirrhinum majus*) which contains a dimerization domain and a Zinc finger-DNA binding domain and thus is potentially an autonomous element (SEQ ID NO:24). The nucleic acids sequence of the Arlecchino Psy1 gene (SEQ ID NO:5) is presented in FIG. 8.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

---

The invention claimed is:

1. A tomato cultivar producing fruit having an Arlecchino phenotype of yellow-red segments spanning from the placenta and/or locules across the fruit pericarp to the epidermis, wherein
   cells of the yellow segments are homozygous for an allele of $r^{arl}$, the $r^{arl}$ allele is Phytoene synthase 1 (Psy1) allele comprising an insertion within an intron of the allele, wherein the insertion comprises a transposon within intron 8 of the allele, comprising a nucleic acid sequence having at least 90% sequence identity to SEQ ID NO:3, and flanked at the 3' end by a nucleic acid sequence selected from the group consisting of SEQ ID NO:1 and SEQ ID NO:2, and wherein the insertion results in a non-functional splice variant of Psy1; and
   cells of the red segments comprise:
   a. at least one wild type Psy1 allele;
   b. at least one Psy1 allele comprising transposon excision footprint, the transposon excision footprint comprising at least one nucleotide deletion within the nucleic acid sequence set forth in SEQ ID NO:7; or
   c. a combination of a and b.

2. The tomato plant of claim 1, wherein the $r^{arl}$ allele comprises the nucleic acid sequence set forth in SEQ ID NO:5.

3. The tomato plant of claim 1, said plant produces cherry tomatoes.

4. The tomato plant of claim 1, said plant further comprises within its genome an additional Psy1 mutant allele encoding for a yellow flesh phenotype, the mutant allele comprising a nucleic acid sequence selected from the group consisting of SEQ ID NO:8 and SEQ ID NO:9.

5. A seed of the tomato plant of claim 1, wherein a plant grown from the seed produces fruit having a phenotype of yellow-red segments spanning from the placenta and/or locules across the fruit pericarp to the epidermis, wherein
   cells of the yellow segments are homozygous for an allele of $r^{arl}$, the $r^{arl}$ allele is Phytoene synthase 1 (Psy1) allele comprising an insertion within an intron of the allele, wherein the insertion comprises a transposon within intron 8 of the allele, comprising a nucleic acid sequence having at least 90% sequence identity to SEQ ID NO:3, and flanked at the 3' end by a nucleic acid sequence selected from the group consisting of SEQ ID NO:1 and SEQ ID NO:2, and wherein the insertion results in a non-functional splice variant of Psy1; and
   cells of the red segments comprise:
   a. at least one wild type Psy1 allele;
   b. at least one Psy1 allele comprising transposon excision footprint, the transposon excision footprint comprising at least one nucleotide deletion within the nucleic acid sequence set forth in SEQ ID NO:7; or
   c. a combination of a and b.

6. A plant part of the tomato plant of claim 1, wherein the plant part is selected from the group consisting of leaves, embryos, roots, root tips, anthers, flowers, isolated cells, isolated tissues thereof, wherein a plant grown from said plant part produces fruit having an Arlecchino phenotype of yellow-red segments spanning from the placenta and/or locules across the fruit pericarp to the epidermis, wherein
   cells of the yellow segments are homozygous for an allele of $r^{arl}$, the $r^{arl}$ allele is Phytoene synthase 1 (Psy1) allele comprising an insertion within an intron of the allele, wherein the insertion comprises a transposon within intron 8 of the allele, comprising a nucleic acid sequence having at least 90% sequence identity to SEQ ID NO:3, and flanked at the 3' end by a nucleic acid sequence selected from the group consisting of SEQ ID NO:1 and SEQ ID NO:2, and wherein the insertion results in a non-functional splice variant of Psy1; and
   cells of the red segments comprise:
   a. at least one wild type Psy1 allele;
   b. at least one Psy1 allele comprising transposon excision footprint, the transposon excision footprint comprising at least one nucleotide deletion within the nucleic acid sequence set forth in SEQ ID NO:7; or c. a combination of a and b.

7. A method for producing a tomato plant producing fruit having an Arlecchino phenotype of yellow-red segments spanning from the placenta and/or locules across the fruit pericarp to the epidermis, the method comprising:
   a. introducing into a tomato plant producing red fruit or a part thereof a genetic element comprising an $r^{arl}$ allele of Phytoene synthase 1(Psy1), wherein the $r^{arl}$ allele comprises an insertion within an intron of the allele, wherein the insertion comprises a transposon within intron 8 of the allele, comprising a nucleic acid sequence having at least 90% sequence identity to SEQ ID NO:3 and flanked at the 3' end by a nucleic acid sequence selected from the group consisting of SEQ ID NO:1 and SEQ ID NO:2, and wherein the insertion results in a non-functional splice variant of Psy1: and
   b. selfing the tomato plant comprising the $r^{arl}$ allele, thereby producing a fruit having the Arlecchino phenotype.

8. The method of claim 7, wherein the genetic element is introduced by crossing the tomato plant producing red fruit with a donor tomato plant comprising the genetic element to provide offspring [cultivated] tomato plants.

9. The method of claim 8, said method further comprises the steps of: a. examining a nucleic acid sample obtained from each offspring cultivated tomato plant or par thereof for the presence of $r^{arl}$ allele; b. selecting offspring tomato plants comprising the $r^{arl}$ allele; and c. examining the fruit produced by the plants selected in step (b) and selecting tomato plants producing fruit having the Arlecchino phenotype.

10. The method of claim 7, wherein the genetic element is introduced by transforming a plurality of cells of the tomato plant producing red fruit with said genetic element.

11. The method of claim 10, said method further comprises: a. examining a nucleic acid sample obtained from each transformed cell for the presence of $r^{arl}$ allele; b. selecting a plurality of cells comprising the $r^{arl}$ allele; c. regenerating the plurality of transformed cells to obtain a plurality of transgenic plants comprising the $r^{arl}$ allele; and d. examining the fruit produced by the transgenic plant and selecting tomato plants producing fruit having the Arlecchino phenotype.

12. The method of claim 9, wherein examining the nucleic acid sample for the presence of the $r^{arl}$ allele is performed by amplifying at least one of an $r^{arl}$ allele marker comprising the nucleic acid sequence set forth in SEQ ID NO:7; a transposon sequence having the nucleic acid sequence set forth in SEQ ID NO:3; the 3' genomic junction of a transposon insertion within the Psy1 allele using a pair of primers comprising the nucleic acid sequence set forth in SEQ ID NO:14 and SEQ ID NO:11; and the 5' genomic junction of a transposon insertion within the Psy1 allele using a pair of primers comprising the nucleic acid sequence set forth in SEQ ID NO:15 and SEQ ID NO:16.

13. The method of claim 11, wherein examining the nucleic acid sample for the presence of the $r^{arl}$ allele is performed by amplifying at least one of an $r^{arl}$ allele marker comprising the nucleic acid sequence set forth in SEQ ID NO:7; a transposon sequence having the nucleic acid sequence set forth in SEQ ID NO:3; the 3' genomic junction of a transposon insertion within the Psy1 allele ; and the 5' genomic junction of a transposon insertion within the Psy1 allele using a pair of primers comprising the nucleic acid sequence set forth in SEQ ID NO:14 and SEQ ID NO:11; and the 5' genomic junction of a transposon insertion within the Psy1 allele using a pair of primers comprising the nucleic acid sequence set forth in SEQ ID NO:15 and SEQ ID NO:16.

* * * * *